(12) United States Patent
Okamoto et al.

(10) Patent No.: US 11,559,543 B2
(45) Date of Patent: Jan. 24, 2023

(54) IMMUNOSTIMULATOR, PHARMACEUTICAL COMPOSITION, AND FOOD OR BEVERAGE

(71) Applicant: ZENOGEN PHARMA CO., LTD., Fukushima (JP)

(72) Inventors: Etsuya Okamoto, Fukushima (JP); Hiroaki Kodama, Fukushima (JP)

(73) Assignee: ZENOGEN PHARMA CO., LTD., Fukushima (JP)

( * ) Notice: Subject to any disclaimer, the term of this patent is extended or adjusted under 35 U.S.C. 154(b) by 300 days.

(21) Appl. No.: 16/321,781

(22) PCT Filed: Aug. 2, 2017

(86) PCT No.: PCT/JP2017/028112
§ 371 (c)(1),
(2) Date: Jan. 29, 2019

(87) PCT Pub. No.: WO2018/025926
PCT Pub. Date: Feb. 8, 2018

(65) Prior Publication Data
US 2021/0069234 A1  Mar. 11, 2021

(30) Foreign Application Priority Data

Aug. 4, 2016  (JP) .............................. JP2016-154015

(51) Int. Cl.
| | | |
|---|---|---|
| A61K 31/722 | (2006.01) | |
| A61P 37/04 | (2006.01) | |
| A61K 9/14 | (2006.01) | |
| A61K 47/12 | (2006.01) | |
| A61K 47/24 | (2006.01) | |

(52) U.S. Cl.
CPC .............. *A61K 31/722* (2013.01); *A61K 9/14* (2013.01); *A61K 47/12* (2013.01); *A61K 47/24* (2013.01); *A61P 37/04* (2018.01)

(58) Field of Classification Search
None
See application file for complete search history.

(56) References Cited

U.S. PATENT DOCUMENTS

| | | | |
|---|---|---|---|
| 4,975,542 A | | 12/1990 | Hirayama et al. |
| 5,611,971 A | * | 3/1997 | Maedera ............... A61K 9/1694 264/4.1 |
| 8,431,160 B2 | * | 4/2013 | O'Hagan ................ A61P 35/00 424/193.1 |
| 2008/0292663 A1 | * | 11/2008 | Gerber .................... A61K 47/32 424/280.1 |
| 2010/0048508 A1 | | 2/2010 | Ben-shalom |
| 2010/0144945 A1 | * | 6/2010 | Nakazawa ............. C09D 5/082 524/417 |
| 2014/0107015 A1 | | 4/2014 | Kim et al. |
| 2015/0224044 A1 | * | 8/2015 | Baker ..................... A61P 31/04 424/49 |

FOREIGN PATENT DOCUMENTS

| | | | |
|---|---|---|---|
| JP | 1-301701 | 12/1989 | |
| JP | 2009-29714 | 2/2009 | |
| JP | 2009-29715 | 2/2009 | |
| JP | 2010-511403 | 4/2010 | |
| JP | 2010-180377 | 8/2010 | |
| JP | 2011-132369 | 7/2011 | |
| WO | WO-2008068763 A2 * | 6/2008 | ............... A61P 3/06 |

OTHER PUBLICATIONS

Janciauskaite, U., Rakutyte, V., Miskinis, J., & Makuska, R. (2008). Synthesis and properties of chitosan-N-dextran graft copolymers. Reactive and Functional Polymers, 68(3), 787-796. (Year: 2008).*
Al-Kassas, R., Wen, J., Cheng, A. E. M., Kim, A. M. J., Liu, S. S. M., & Yu, J. (2016). Transdermal delivery of propranolol hydrochloride through chitosan nanoparticles dispersed in mucoadhesive gel. Carbohydrate polymers, 153, 176-186. (Year: 2016).*
Kim, M. K., Lee, J. S., Kim, K. Y., & Lee, H. G. (2013). Ascorbyl palmitate-loaded chitosan nanoparticles: characteristic and polyphenol oxidase inhibitory activity. Colloids and Surfaces B: Biointerfaces, 103, 391-394. (Year: 2012).*
Samer S. El-Kamary et al: "Adjuvanted Intranasal Norwalk . . . " Journal of Infectious Diseases, vol. 22, No. 11, Dec. 1, 2010, pp. 1649-1658.
Kai Zhao et al: "Preparation and immunological effectiveness of . . ." Vaccine, vol. 29, No. 47, Sep. 9, 2011, pp. 8549-8556.
Illum L et al: "Chitosan as a Delivery System for Vaccines" Advanced Drug Delivery Reviews, vol. 51, No. 1-03, Sep. 23, 2001, pp. 81-96.
Erdal Cevher et al: "Development of chitosan-pullulan composite nanoparticles . . . " Journal of Microencapsulation, vol. 32, No. 8, Nov. 17, 2015, pp. 769-783.
EESR, EP Patent Application No. 17837028.4, mailed Feb. 26, 2020, 5 pages.
Peretz et al., "Chitosan/anionic surfactant microparticles synthesized by high pressure saraying method for removal of phenolic pollutants", Central European Journal of Chemistry, 10(6), 2012, pp. 1969-1979.
Office Action for EP Patent Application No. 17837028.4, dated Aug. 24, 2020, 4 pages.
Office Action for JP 2018-531958, dated Jul. 9, 2019, 5 pages.
Chang, et al., "Components Simulation of Viral Envelope via Amino Acid Modified Chitosans for Efficient Nucleic Acid Delivery: In Vitro and Vivo Study", Adv Funct Mater., 2013, vol. 23, p. 2691-2699.

(Continued)

*Primary Examiner* — Dale R Miller
(74) *Attorney, Agent, or Firm* — Casimir Jones, SC; Robert A. Goetz

(57) ABSTRACT

Provided is an immunostimulator containing: chitosan and/or a chitosan derivative each having a weight-average molecular weight of 10k to 1000k; and an anionic surfactant, the immunostimulator being in particulate form. Also provided are a pharmaceutical composition and an alimentary product, each containing the immunostimulator as an active ingredient.

7 Claims, 10 Drawing Sheets

(56) References Cited

OTHER PUBLICATIONS

Petrov, et al., "Chitosan-Dextran Branched Copolymers: Synthesis and Properties", Natural Polymers, 2014, vol. 56 No 3, p. 341-351.
Proceedings of 14th Annual Meeting of Japan Society for Food Engineering, 2013, p. 33, 6-1A-6.
The Pharmaceutical Society of Japan, the 133th Annual Meeting, 2013, 28pmF-130S, 5 pages.
Hafner, Anita, Short- and Long-Term Stability of Lyophilised Melatonin-Loaded Lecithin/Chitosan Nanoparticles, Chem Pharm Bull., Sep. 2011, p. 1117-1123.
Urakami Foundation Research Report, 2015, vol. 22, pp. 16-21.
Office Action For JP Patent Application No. 2018-531958, dated Nov. 19, 2019, 8 pages.
Ishikawa, K., Mar. 2007, p. 63-66, "Vaccine adjuvant development and animal testing".
Ishikawa, K., Mar. 2006, p. 39-42, "Studies on adjuvant and DDS for development of IgA-inducing HIV-I vaccine".
Xu, Y. et al., "Effect of molecular structure of chitosan on protein delivery properties of chitosan nanoparticles" Int. J. Pharm., vol. 250, pp. 215-226, 2003.
Yalpani, M. and Hall, L., "Some Chemical and Analytical Aspects of Polysaccharide Modifications . . . " Macromolecules, vol. 17, pp. 272-281, 1984.
English translation of International preliminary report on patentability of PCT/JP2017/028112, dated Feb. 5, 2019, 10 pages.
International Search Report for PCT/JP2017/028112, dated Sep. 12, 2017, 2 pages.

* cited by examiner

Group 1: Chitosan derivative (amino group)-to-additive (carboxyl group) mixing ratio 1/0.28
Group 2: Chitosan derivative (amino group)-to-additive (carboxyl group) mixing ratio 1/1
Group 3: Chitosan derivative (amino group)-to-additive (carboxyl group) mixing ratio 1/7

IMMUNOSTIMULATOR, PHARMACEUTICAL COMPOSITION, AND FOOD OR BEVERAGE

TECHNICAL FIELD

The present invention relates to an immunostimulator, a pharmaceutical composition, and an alimentary product.

BACKGROUND ART

Various kinds of substance have been known to be useful as immunologic adjuvants for use in vaccination. For example, many polysaccharides are known to have adjuvanticity, among which chitin and chitosan have been proven to be especially useful. These chitin and chitosan are similar in structure to peptidoglycan that forms bacterial cell walls, and are substantially harmless because they are degraded by a biological defense mechanism. A wound dressing, making use of the biocompatibility of chitin, has also been in practical use. On the other hand, chitin and chitosan are known to activate the immune system even alone as a nonself in animal bodies, and this contributes to the adjuvant effect of chitin and chitosan. Chitosan, which contains free amino groups, is cationized and becomes soluble under acidic conditions, and therefore is capable of forming a complex via an electrostatic interaction with an anionic substrate (such as protein or nucleic acid). Every kind of cell has an anionically charged surface; therefore, chitosan strongly binds to the cell surface and mucous membranes in living bodies. As such, it is inferred that chitosan, which has properties of becoming cationized, is more suitable as an immunologic adjuvant.

Note here that one problem in using chitosan as an immunologic adjuvant is its high level of crystallinity. For example, even in a case where chitosan is once dissolved in a solvent under acidic conditions, the chitosan molecules, upon introduction into the living body, lose their charge because of a pH increase that they experience in the living body, and therefore their crystallization proceeds and the molecules separate out as microparticles or turn into a gel. Furthermore, it is inferred that, even in a case of a complex of chitosan and some other substance such as protein obtained in a solution, the dissociation of the complex also proceeds as the crystallization proceeds. To date, various kinds of chitosan derivatives obtained by modifying the properties of chitosan have been reported, as disclosed in Non-patent Literature 1. Furthermore, Patent Literature 1 discloses a branched chitosan derivative composed of a chitosan backbone with chitosan side chains, which has been developed to achieve both water solubility and functionality such as low viscosity. Patent Literature 2 discloses an aqueous immunologic adjuvant solution containing cationized chitosan.

A technique of using chitosan in the form of microparticles is also known. Patent Literature 3 discloses an immunologic adjuvant dispersion containing chitosan microparticles. Non-patent Literature 2 discloses use of chitosan, which has been micronized with use of tripolyphosphoric acid, as a drug delivery carrier. It has also been known that, when microparticles containing an antigen are taken up by macrophages, an immune response specific to the antigen proceeds.

In many cases, chitosan microparticles are prepared by mixing with a polyanion such as tripolyphosphoric acid or hyaluronic acid. There have been many reports on examples of development of chitosan microparticles complexed via an electrostatic interaction.

CITATION LIST

Patent Literatures

[Patent Literature 1]
Japanese Patent Application Publication Tokukai No. 2011-132369 (Publication date: Jul. 7, 2011)
[Patent Literature 2]
Japanese Patent Application Publication Tokukai No. 2009-29715 (Publication date: Feb. 12, 2009)
[Patent Literature 3]
Japanese Patent Application Publication Tokukai No. 2009-29714 (Publication date: Feb. 12, 2009)
[Non-Patent Literatures]
[Non-patent Literature 1]
Yalpani and Hall, Macromolecules, vol. 17, pp. 272-281, 1984
[Non-patent Literature 2]
Xu et al., Int. J. Pharm., vol. 250, pp. 215-226, 2003

SUMMARY OF INVENTION

Technical Problem

However, none of those discussed above have been adopted in practical use as an adjuvant that induces an immune response. The effects of those discussed above are far from satisfactory also in comparison with Freund's adjuvant used in animal testing. For the usefulness and immunostimulatory effect of chitosan as an immunologic adjuvant to be enhanced and improved, there is a demand for development of a novel amorphous chitosan derivative and novel micronized chitosan, by utilizing the foregoing characteristics of chitosan.

Solution to Problem

The inventors have diligently studied in view of the above circumstances, and found that a chitosan derivative having a certain structure has stronger immunostimulatory activity. The inventors further found that, by micronizing chitosan or a chitosan derivative having a weight-average molecular weight falling within a certain range with use of an anionic surfactant, it is possible to obtain microparticles with a high level of immunostimulatory activity. The inventors then arrived at a chitosan derivative, an immunostimulator containing a chitosan derivative, a pharmaceutical composition containing the immunostimulator as an active ingredient, and an alimentary product containing the immunostimulator, of the present invention.

In order to solve the foregoing problem, the present invention encompasses one aspect stated below.

An immunostimulator containing: chitosan and/or a chitosan derivative each having a weight-average molecular weight of 10 k to 1000 k; and an anionic surfactant, the immunostimulator being in particulate form.

Advantageous Effects of Invention

The present invention brings about an effect of making it possible to provide a chitosan derivative having immunostimulatory activity, an immunostimulator containing the chitosan derivative, a pharmaceutical composition containing the immunostimulator as an active ingredient, and an alimentary product containing a chitosan derivative.

DESCRIPTION OF EMBODIMENTS

Figure 1:
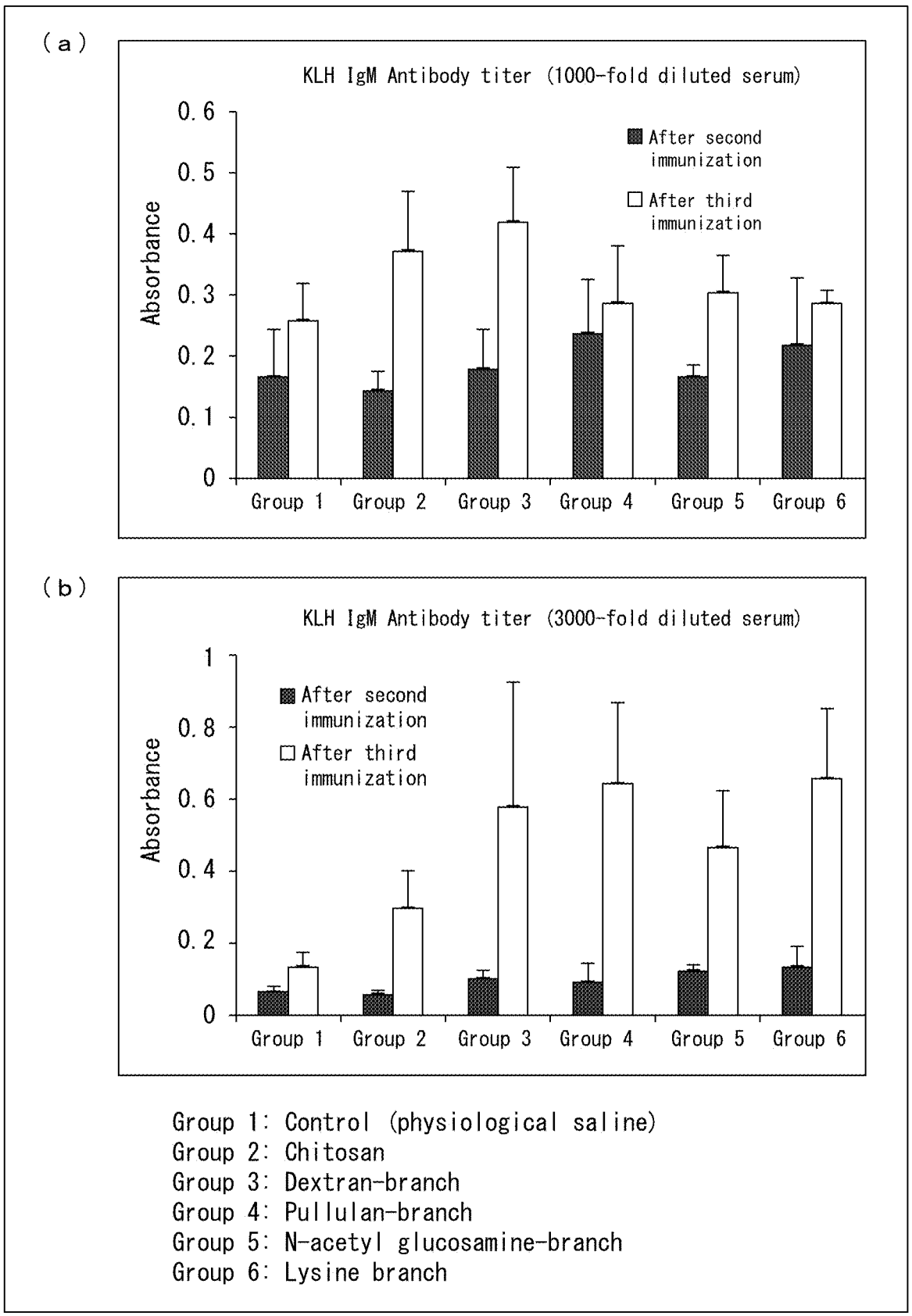
FIG. 1 shows antibody titers after the intraperitoneal administration of chitosan derivatives to mice, in accordance with Example 2 of the present invention.

The following description will discuss embodiments of the present invention in detail.

[Definitions of Terms and the Like]

As used herein, the term "chitosan derivative" refers to a compound in which saccharide units of chitosan forms a main chain and the main chain has side chains.

As used herein, the term "degree of branching" refers to the ratio of the number of saccharide units with side chains to the total number of the saccharide units of chitosan. In this specification, the "degree of branching" is represented as the parameter z. The details of the parameter z will be described later.

As used herein, the term "degree of deacetylation" indicates how much percentage of the acetylamino groups bound to carbon at 2-positions of saccharide units of chitosan have been deacetylated into free amino groups.

As used herein, the "degree of substitution" with side chain indicates the extent to which the amino groups bound to carbon at 2-positions of the saccharide units of chitosan are substituted by side chains. This is expressed in ratio of substituted amino groups to the sum of free amino groups and the substituted amino groups bound to carbon at 2-positions of the saccharide units of chitosan. The degree of substitution can be represented by the following equation: Degree of substitution=Number of side-chain-substituted amino groups in saccharide units of chitosan/(Number of free amino groups+Number of side-chain-substituted amino groups) in saccharide units of chitosan.

As used herein, the term "particulate" or "microparticles" refers to particles having a particle size of not greater than several tens of micrometers.

As used herein, the term "immunostimulator" refers to a molecule, a substance, or a composition each of which has the ability to specifically or non-specifically change, increase, induce, reinduce, enhance, or initiate an antigen-specific immune response. The immunostimulator in accordance with the present invention encompasses those that are capable of enhancing either humoral immunity or cell-mediated immunity and those that are capable of enhancing both humoral immunity and cell-mediated immunity. The "immunostimulator" in this specification may also be referred to as "adjuvant" or "immunologic adjuvant".

As used herein, the term "subject" refers to a subject that receives administration of a chitosan derivative, an immunostimulator, a pharmaceutical composition, or an alimentary product, in accordance with the present invention.

As used herein, the term "prophylactically treating" refers to preventing the development of a disease, an illness, or a disorder. The term "therapeutically treating" refers to alleviating or eliminating the developed disease, illness, or disorder or the symptoms accompanying the developed disease, illness, or disorder.

[1. Chitosan Derivative]

The following description will discuss a chitosan derivative in accordance with the present invention.

In one embodiment of the present invention, the following chitosan derivative is provided.

A chitosan derivative having immunostimulatory activity, the chitosan derivative being represented by the following General Formula (I):

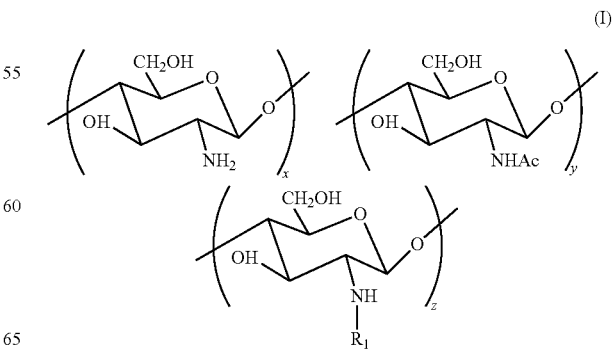

where x, y, and z represent molar proportions which satisfy the equation x+y+z=1, where 0≤x<1, 0≤y<1, and 0<z≤1, and where $R^1$ is a pullulan side chain represented by the following General Formula (II):

(II)

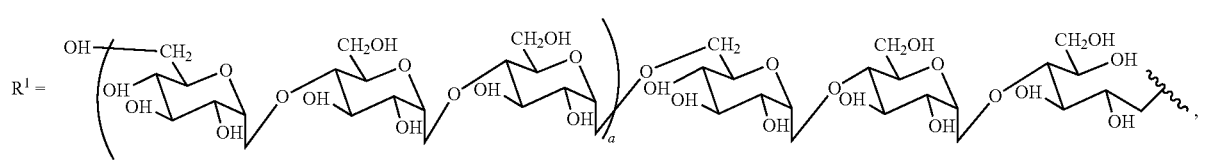

a dextran side chain represented by the following General Formula (III):

(III)

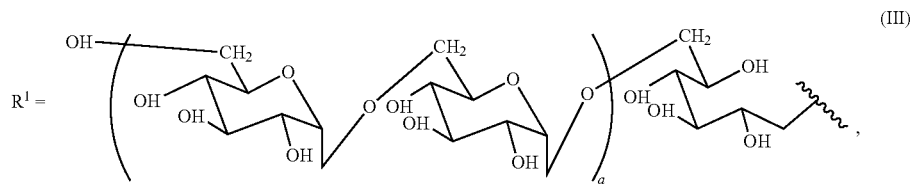

a glucosamine side chain represented by the following General Formula (IV):

(IV)

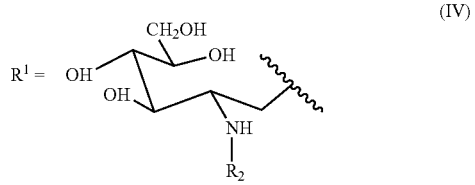

where $R^2$ is an acetyl group, a lysine side chain represented by the following General Formula (V):

(V)

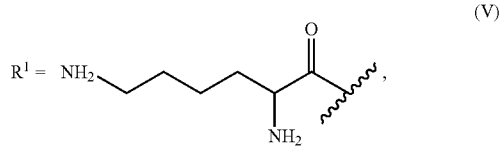 [SMILES: *C(=O)C(N)CCCCN]

or a lactose side chain represented by the following General Formula (VI):

(VI)

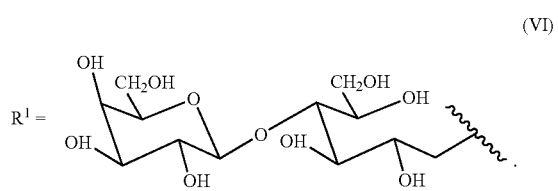 [SMILES: *CC(O)C(O)C(OC1OC(CO)C(O)C(O)C1O)C(O)CO]

As such, the chitosan derivative of the present invention is structured such that: a saccharide with a free carboxyl end group is bound, via a Schiff base by reductive alkylation, to the amino group bound to carbon at 2-position of a glucosamine unit constituting a saccharide unit of chitosan; or an amino acid with a free carboxyl end group forms an amide bond with the amino group bound to carbon at 2-position of a glucosamine unit constituting a saccharide unit of chitosan through a condensation reaction.

(Parameters of Chitosan Main Chain)

The values of the foregoing parameters x and y differ depending on the type of chitosan (source material) for use in the production of the chitosan derivative of the present invention. The values of the foregoing parameters x and y can be adjusted by acetylating or deacetylating chitosan as a source material or the resulting chitosan derivative. Note that chitosan as a source material will be described in the following (Chitosan) section. The parameter z indicates the ratio of saccharide units with side chains to the saccharide units of chitosan. The value of z can be represented by the following equation: z=(Number of saccharide units with side chains in chitosan derivative)/(Total number of saccharide units of chitosan derivative). The value of z can be controlled by adjusting the amount of chitosan that will become a main chain and the amount of a compound that will become a side chain.

(Length of Chitosan Main Chain)

The chitosan derivative in accordance with the present invention includes, as a main chain, chitosan that contains saccharide units composed of: glucosamine unit; N-acetyl glucosamine unit; and glucosamine unit having the foregoing $R^1$ group bound to N that is bound to carbon at 2-position of the glucosamine unit. The number of the saccharide units constituting the chitosan main chain is preferably 30 to 12,000, more preferably 60 to 6,000, even more preferably 120 to 3000.

(Length of Side Chain and Degree of Substitution)

The chitosan derivative in accordance with the present invention contains hydrophilic side chains, and therefore has an improved solubility in a wider pH range as compared to chitosan alone with no side chains. For example, the chitosan derivative in accordance with the present invention has a high level of water solubility even in the pH range of from 6.5 to 8.0. The degree of substitution, which indicates the extent to which the amino groups at 2-positions of the saccharide units of the chitosan main chain are substituted by side chains, can be appropriately selected according to the type of chitosan derivative and the final use of the chitosan derivative. For example, in a case where the chitosan derivative is for use in an immunologic adjuvant, the degree of substitution is preferably 0.005 to 0.5, more preferably 0.005 to 0.3. The degree of substitution may be determined based on a known technique (e.g., sugar composition analysis), and may be calculated, for example, by NMR spectrometry.

The chitosan derivative of the present invention can alternatively be designed such that, by addition, substitution, or the like of a functional group or molecule to impart some other activity or some other function to the chitosan derivative, the chitosan derivative is modified to have that activity or function additionally. Such further modification can be made at a position and in a manner such that, even after the modification, the characteristics or physical properties of the original, unmodified chitosan derivative are maintained. One example of the modification is amidation of 4-maleimide butyric acid and the amino group bound to carbon at 2-position of a saccharide unit of the chitosan main chain in the chitosan derivative. With this modification, it is possible, for example, to subject the chitosan derivative of the present invention to coupling with a cysteine-containing peptide.

In the chitosan derivative of the present invention, in a case where $R^1$ is the pullulan side chain represented by the foregoing Formula (II), a is preferably 20 to 600, more preferably 50 to 300. The degree of substitution with the pullulan side chain is preferably 0.001 to 0.1, more preferably 0.002 to 0.05.

In the chitosan derivative of the present invention, in a case where $R^1$ is the dextran side chain represented by the foregoing Formula (III), a is preferably 15 to 300, more preferably 30 to 200. The degree of substitution with the dextran side chain is preferably 0.001 to 0.1, more preferably 0.002 to 0.05.

In the chitosan derivative of the present invention, in a case where $R^1$ is the glucosamine side chain represented by the foregoing Formula (IV), the degree of substitution with the glucosamine side chain is preferably 0.05 to 0.5, more preferably 0.1 to 0.3. The $R^2$ groups, the same or different, may be H, acetyl group, or the $R^1$ group, and preferably all acetyl groups.

In the chitosan derivative of the present invention, in a case where $R^1$ is the lysine side chain represented by the foregoing Formula (V), the degree of substitution with the lysine side chain is preferably 0.02 to 0.5, more preferably 0.05 to 0.3. The chitosan derivative may be structured such that: another lysine with a free carboxyl end group forms an amide bond with the amino group bound to carbon at 2-position of the lysine side chain represented by $R^1$ through a condensation reaction; and thereby at least one lysine molecule is additionally attached.

(pH Range within which Chitosan Derivative is Soluble)

As described earlier, chitosan, which has a degree of deacetylation of 70% or greater, is soluble in the acidic pH region of 6 and lower. On the other hand, the chitosan derivative of the present invention is soluble in a wider pH range than chitosan, and is soluble even in the neutral to alkaline pH region of from 6.5 to 8.0. In one embodiment, usually the chitosan derivative of the present invention is preferably used under the condition of a pH of up to 8.0 or lower, even more preferably used at a pH of 5.0 to 7.5.

A chitosan derivative in accordance with one embodiment of the present invention is a chitosan derivative that contains a pullulan side chain. As will be described later in the (Saccharide contained as side chain) section, pullulan is soluble in water and, despite its low viscosity, has excellent lubricity and adhesiveness. In a case where the side chain is a pullulan side chain, the chitosan derivative is highly soluble and is particularly suitable as a soluble adjuvant.

A chitosan derivative in accordance with one embodiment of the present invention is a chitosan derivative that contains a glucosamine side chain or a dextran side chain. Glucosamine and dextran are biodegradable. Therefore, the chitosan derivative containing such a side chain is highly safe and is particularly suitable as a component of an immunologic adjuvant for introduction into the living body.

A chitosan derivative in accordance with one embodiment of the present invention is a chitosan derivative that contains a lysine side chain. In a case where the side chain is a lysine side chain, the chitosan derivative remains in a cationized state even in blood plasma having a pH of 7.4, and is particularly suitable as a particulate adjuvant.

In the production of the chitosan derivative in accordance with the present invention, chitosan is used as a material for the main chain, and a compound such as a saccharide or an amino acid is used as a material for the side chain. The following description will discuss the compounds serving as materials for the chitosan derivative of the present invention one by one.

(Chitosan)

Usually, chitosan can be prepared by deacetylating chitin (poly-β-1,4-N-acetyl glucosamine) derived from the exoskeleton of crabs or shrimp by treating it with an alkali, enzyme, or the like. In this specification, chitin at least partially deacetylated is referred to as chitosan. Note that chitosan in accordance with the present invention is not limited to naturally-occurring ones and may be a chemically synthesized one. Chitosan used as a material for the chitosan derivative in accordance with the present invention is such that the percentage of N-deacetylated units of the glucosamine units constituting the chitin molecule, that is, degree of deacetylation, is preferably in the range of from 60 to 100%, more preferably 70 to 100%. Note that the degree of deacetylation may be determined based on a known technique (e.g., colloid titration method). One example of the known technique is NMR.

Alternatively, a naturally-occurring chitosan molecule having a large molecular weight, which is composed of a large number of saccharide residues, may be hydrolyzed and thereby processed into a chitosan molecule with a desired molecular weight.

As described earlier, the chitosan main chain of the chitosan derivative is composed of 30 to 12,000 constituent saccharide units. Thus, the weight-average molecular weight of chitosan as a source material can be about 5 k (5,000) to about 2000 k (2,000,000), assuming that the molecular weight of each glucosamine residue of chitosan is 161, that the molecular weight of each N-acetyl glucosamine residue is 203, and that the degree of deacetylation falls within the range of from 60 to 100%.

The starting material of the chitosan derivative of the present embodiment is not particularly limited as to the form of chitosan molecules, and may be, for example, chitosan molecules in the form of powder, fibers, a film, a sheet, a hydrogel, or a solution.

(Saccharide Contained as Side Chain)

A chitosan derivative in accordance with one embodiment of the present invention is composed of a chitosan main chain with a saccharide side chain. Examples of a saccharide chain with a reducing end, which can be used to obtain the chitosan derivative, include those derived from aldoses and those derived from ketoses, in each of which one or more constituent saccharide units are contained. More specific examples of the saccharide include monosaccharides such as: pentoses and hexoses, e.g., glucose, fucose, mannose, arabinose, galactose, xylose, erythrose, heptulose, hexulose, pentulose, and the like; amino sugars such as glucosamine, N-acetyl glucosamine (e.g., N-acetyl-D-glucosamine), and galactosamine; and saccharide derivatives such as uronic acids and deoxysugars. Specific examples of the saccharide further include disaccharides and polysaccharides each composed of a saccharide chain which is a combination of any of the above-listed monosaccharides as constituents, such as: maltose, isomaltose, lactose, melibiose, and maltotriose; and various oligosaccharides. Specific examples of the saccharide further include: natural polysaccharides such as pullulan, inulin, amylose, amylopectin, dextran, dextrin, and starch; and degraded or isomerized versions thereof and derivatives thereof. One or more of these saccharides in combination can be used in the production. These saccharides as source materials may be in the form of a hydrate. Among those listed above, especially N-acetyl glucosamine (e.g., N-acetyl-D-glucosamine), dextran, and pullulan are suitable as a saccharide for use in the chitosan derivative in accordance with the present invention. Pullulan is soluble in water and, despite its low viscosity, has excellent lubricity and adhesiveness, and therefore used as a food additive such as a thickener or a stabilizer. Glucosamine and dextran are biodegradable, and therefore especially suitable for use as a component of an immunologic adjuvant for application to the living body.

In a case where melibiose is contained as the side chain, the chitosan derivative in accordance with the present invention contains the melibiose side chain represented by the following Formula (VII):

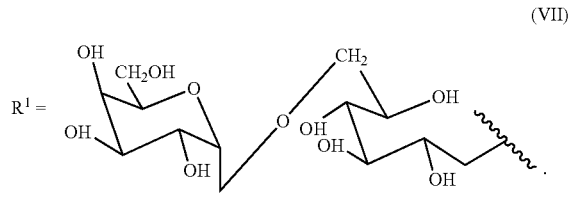 [SMILES: *CC(O)C(O)C(O)C(O)COCC1OC(CO)C(O)C(O)C1O]

(VII)

(Amino Acid or Amino Acid Derivative Contained as Side Chain)

A chitosan derivative in accordance with another embodiment of the present invention is composed of a chitosan main chain with an amino acid side chain. Examples of the amino acid side chain or amino acid derivative side chain with a reducing end, which is used to obtain the chitosan derivative, include lysine (e.g., L-lysine), carnitine, arginine, proline, and histidine. Among these, especially lysine and carnitine are suitable as an amino acid for use in the chitosan derivative in accordance with the present invention. In a case where carnitine is introduced as the side chain, the chitosan derivative in accordance with the present invention contains the carnitine side chain represented by the following Formula (VIII):

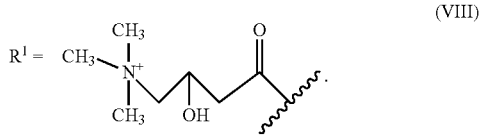 [SMILES: *C(=O)CC(O)C[N+](C)(C)C]

(VIII)

A chitosan derivative in accordance with a further embodiment of the present invention is composed of a chitosan main chain with two or more different kinds of saccharide and/or amino acid side chains.

(Other Compound Introduced as Side Chain)

A chitosan derivative in accordance with still a further embodiment of the present invention is composed of chitosan with a polyethylene glycol side chain. Examples of a compound with a reducing end, which can be used to obtain the chitosan derivative, include methoxy PEG-aldehyde.

(Method of Producing Chitosan Derivative)

<Method of Producing Chitosan Derivative whose Side Chain is Saccharide>

A chitosan derivative in accordance with the present embodiment can be produced by a known production method. For example, in cases where the side chain of the chitosan derivative is a saccharide, a method of producing the chitosan derivative in accordance with the present embodiment involves: a chitosan dissolving step including dissolving chitosan to prepare a chitosan solution; a saccharide dissolving step including adding and dissolving a saccharide in the chitosan solution; and a reducing agent adding step including further adding a reducing agent after the saccharide dissolving step.

A reaction that takes place in the production method in cases where the side chain of the chitosan derivative is a saccharide is generally such that: the saccharide is bound, via a Schiff base, to the amino group bound to carbon at 2-position of a glucosamine unit constituting chitosan, through reductive N-alkylation.

<Chitosan Dissolving Step>

The chitosan dissolving step is a step of dissolving chitosan to prepare a chitosan solution. In one embodiment, the chitosan dissolving step involves dispersing chitosan in water and then adding acetic acid to thereby dissolve chitosan. Note that, before or concurrently with the chitosan dissolving step, a step of partially deacetylating chitin may be carried out. The partial deacetylation reaction may be carried out by a known de-N-acetylation method.

<Saccharide Dissolving Step>

The saccharide dissolving step is a step of further adding and dissolving a saccharide in the chitosan solution after the chitosan dissolving step. The saccharide dissolving step may be carried out concurrently with the chitosan dissolving step. That is, the saccharide may be added to the solvent together with chitosan.

<Reducing Agent Adding Step>

The reducing agent adding step is a step of adding a reducing agent after the saccharide dissolving step. The reducing agent used here can be, in cases where the side chain of the chitosan derivative is a saccharide, 2-picoline borane, sodium cyanoborohydride (NaCNBH$_3$), an amine-borane-based reducing agent such as ammonia borane (NH$_3$BH$_3$) or monomethyl amine borane (CH$_3$(NH$_2$BH$_3$)), or the like, among which 2-picoline borane is preferred. After the addition of the reducing agent, the solution is stirred at room temperature, and thereby a reaction is allowed to take place. The reaction time is, for example, 2 hours to several days, or 6 hours to 24 hours, and, for better work efficiency, not more than 20 hours. The <Reducing agent adding step> may be carried out concurrently with the <Chitosan dissolving step> and/or the <Saccharide dissolving step>.

<Method of Producing Chitosan Derivative whose Side Chain is Amino Acid>

Another example of a method of producing a chitosan derivative in accordance with the present embodiment, in cases where the side chain of the chitosan derivative is an amino acid, is a method that involves: a chitosan dissolving step including dissolving chitosan to prepare a chitosan solution; an amino acid dissolving step including adding and dissolving an amino acid in the chitosan solution; and a condensing agent adding step including further adding a condensing agent after the amino acid dissolving step.

A reaction that takes place in the production method in cases where the side chain is an amino acid is generally such that: an amide bond is formed through a condensation reaction caused by the condensing agent between (i) the amino group bound to carbon at 2-position of glucosamine which is a constituent saccharide unit of chitosan and (ii) the amino acid such as lysine or carnitine with a free carboxyl end group.

<Chitosan Dissolving Step>

The chitosan dissolving step is the same as that of the aforementioned method of producing a chitosan derivative in cases where the side chain is a saccharide.

<Amino Acid Dissolving Step>

The amino acid dissolving step is a step of further adding and dissolving an amino acid in the chitosan solution after the chitosan dissolving step. The amino acid dissolving step may be carried out concurrently with the chitosan dissolving step. That is, the amino acid may be added to the solvent together with chitosan.

<Condensing Agent Adding Step>

The condensing agent adding step is a step of adding a condensing agent after the amino acid dissolving step. The condensing agent used here can be, in cases where the side chain is an amino acid, 4-(4,6-dimethoxy-1,3,5-triazine-2-yl)-4-methylmorpholinium chloride, 1-ethyl-3-(3-dimethylaminopropyl) carbodiimide hydrochloride, or the like, among which 4-(4,6-dimethoxy-1,3,5-triazine-2-yl)-4-methylmorpholinium chloride is preferred. After the addition of the condensing agent, the solution is stirred at room temperature, and thereby a reaction is allowed to take place. The reaction time is, for example, 4 hours to several days, or 6 hours to 24 hours, and, for better work efficiency, not more than 12 hours. The <Condensing agent adding step> may be carried out concurrently with the <Chitosan dissolving step> and/or the <Amino acid dissolving step>.

The chitosan derivative thus obtained can be purified in accordance with a known method such as using ultrafiltration, washing with solvent, purification by precipitation, gel filtration, ion-exchange column chromatography, charcoal column chromatography, cellulose dialysis membrane, electrodialysis, or the like. The chitosan derivative of the present invention can be processed into a powder form, a solution form, a suspension form, or the like, based on a known method. The obtained chitosan derivative can also be dried using an appropriate drying means, such as freeze drying, for preservation in dry condition, if necessary.

As will be described also in the following Examples, the chitosan derivative of the present intention has a remarkable living body's immune system activating effect, that is, a remarkable immunostimulatory effect. Thus, the chitosan derivative of the present intention can be suitably used as an immunostimulator that is safe and effective. Furthermore, the chitosan derivative in accordance with the present intention is soluble even in the neutral to alkaline pH region of from 6.5 to 8.0. Thus, the chitosan derivative of the present intention is safe even to the living body and is usable in a wider range of applications than conventional chitosan and modified chitosans.

[2. Immunostimulator]

(Immunostimulator that Contains Chitosan Derivative)

The following description will discuss an immunostimulator in accordance with the present invention. In one embodiment, the immunostimulator of the present invention contains, as an active ingredient, at least one chitosan derivative represented by the foregoing General Formula (I). In another embodiment, the immunostimulator of the present invention may contain a combination of two or more chitosan derivatives represented by the foregoing General Formula (I). The immunostimulator of the present invention has a remarkable immunostimulatory effect, and thus is useful in therapeutically treating a patient with a disease, illness, or disorder in which normal metabolic and immune responses weaken or are suppressed in the living body. The immunostimulator of the present invention can be used to therapeutically or prophylactically treat a subject such as an animal or human at high risk of developing a disease, illness, or disorder that would result from the condition that adversely affects the immune system.

Furthermore, the inventors have newly found that, by micronizing chitosan or a chitosan derivative having a molecular weight falling within a certain range with use of an anionic surfactant, it is possible to obtain microparticles with a high level of immunostimulatory activity. In one embodiment, the immunostimulator is in particulate form. The following description will discuss an embodiment in which the immunostimulator of the present invention is in particulate form (that is, microparticles serving as immunostimulator) in detail.

(Immunostimulator in Particulate form [Microparticles Serving as Immunostimulator])

The immunostimulator of the present embodiment contains: chitosan and/or a chitosan derivative each having a weight-average molecular weight of 10 k to 1000 k; and an anionic surfactant. The immunostimulator is in particulate form.

The following description will discuss components of the microparticles.

(Components of Microparticles)

<Chitosan and/or Chitosan Derivative>

The weight-average molecular weight of the [chitosan and/or chitosan derivative] contained in the microparticles is 10 k to 1000 k, and is appropriately selected according to the use of the resulting microparticles. The microparticles in the present invention tend to have a greater immunostimulating effect as the molecular weight of chitosan becomes lower.

Note, however, that there is a tendency that a [chitosan and/or chitosan derivative] having a low molecular weight that is equal to or lower than a certain molecular weight, for example, a [chitosan and/or chitosan derivative] having a molecular weight less than 10 k, necessitates relatively complicated production processes. Furthermore, such a [chitosan and/or chitosan derivative] is likely to agglomerate in the solution after the addition of an anionic surfactant. On the other hand, chitosan having a high molecular weight that is equal to or greater than a certain molecular weight, for example, a [chitosan and/or chitosan derivative] having a molecular weight greater than 1000 k, tends to have a high viscosity.

As such, in order to achieve a great immunostimulating effect while offering good handleability, easiness of industrial production, easy availability, and high commercial applicability, the weight-average molecular weight of chitosan or the chitosan derivative for use as a source material in the production of the microparticles is 10 k to 1000 k, more preferably 20 k to 500 k, most preferably 30 k to 100 k.

Furthermore, chitosan for use as a component of the microparticles in accordance with the present invention, or chitosan serving as the main chain of the chitosan derivative, has a degree of deacetylation falling within the range of from preferably 60 to 100%, more preferably from 70 to 100%.

In one embodiment, a chitosan derivative contained in the microparticles can be any of the chitosan derivatives described in the foregoing [1. Chitosan derivative] section or can be a chitosan derivative that contains, as a side chain, any of the structures described in the foregoing (Saccharide contained as side chain), (Amino acid or amino acid derivative contained as side chain), and (Other compound introduced as side chain) sections. For example, the chitosan derivative contains, as a saccharide side chain, a saccharide selected from N-acetyl glucosamine (e.g., N-acetyl-D-glucosamine), dextran, and pullulan. For example, a side chain of the chitosan derivative contained in the microparticles is dextran. Such a chitosan derivative, even before micronization, originally has an immunostimulating effect. Thus, the microparticles, which contain such a chitosan derivative, can achieve a more improved immunostimulatory activity than microparticles of chitosan alone. Furthermore, the microparticles, which contain such a chitosan derivative, have a lower crystallinity than chitosan and are coated with a neutral polysaccharide. Such microparticles are expected to be suppressed from crystallizing and from secondary agglomerating even after micronization, and in turn have improved safety.

In another embodiment, a chitosan derivative contained in the microparticles may be composed of the chitosan main chain with some molecule bound thereto via, for example, covalent bonding, such as a peptide composed of 3 to 150 amino acids, an oligonucleotide, or an oligosaccharide. The molecule bound to the main chain is, for example: a polypeptide coding for any of the antigens described in the following [Antigen] section or a fragment thereof (e.g., epitope); a polynucleotide of a gene coding for the antigenic polypeptide or a fragment thereof; and a peptide having cell adhesion activity or a fragment thereof.

<Anionic Surfactant>

The microparticles of the present invention contain an anionic surfactant. The anionic surfactant contained in the microparticles contains an anionic group and a hydrophobic group. The hydrophobic group is, for example, a substituted or unsubstituted group, and can be a saturated or unsaturated C2-C22 alkyl group.

In one embodiment, the anionic surfactant is at least one selected from the group consisting of phospholipids, C10-C22 fatty acids, and salts of the C10-C22 fatty acids. The anionic surfactant may be a single kind of anionic surfactant or may be a combination of two or more different kinds of anionic surfactant. The microparticles contain (i) a phospholipid or (ii) a C10-C22 fatty acid or a salt thereof, or contain both of (i) and (ii).

[Phospholipid]

Examples of the phospholipids include phosphoglycerides, sphingolipids, cephalin, and mixtures thereof, totally synthetic phospholipids, lecithin, and lysolecithin. Lecithin in the field of chemistry is equivalent to phosphatidylcholine, and thus refers to phosphatidylcholine in this specification. A phospholipid can preferably be lecithin or lysolecithin. More specific examples of the lecithin include soybean lecithin, egg yolk lecithin, hydrogenated soybean lecithin (HSPC), and hydrogenated egg yolk lecithin (HEPC). Examples of the phosphoglycerides include phosphatidylcholine, phosphatidylethanolamine, phosphatidylserine, phosphatidylglycerin, phosphatidylinositol, lysophosphatidylcholine, and phosphatidic acid. Examples of the sphingolipids include sphingomyelin. Note that phospholipids that are not soluble enough in water can be dissolved in an organic solvent such as ethanol and then subjected to the production of microparticles.

[Fatty Acid and Salt thereof]

Fatty acids and salts thereof include C10-C22 fatty acids, salts thereof, and glycerides thereof. A fatty acid may be a saturated fatty acid or an unsaturated fatty acid. The fatty acid or a salt thereof is preferably a C10-C22 fatty acid or a salt thereof, more preferably a C12-C18 fatty acid or a salt thereof.

Examples of the fatty acids include myristic acid, palmitic acid, stearic acid, arachidic acid, behenic acid, lignoceric acid, myristoleic acid, palmitoleic acid, oleic acid, vaccenic acid, icosenoic acid, docosenoic acid, tetracosenoic acid, linoleic acid, α-linolenic acid, icosadienoic acid, icosatetraenoic acid, icosatrienoic acid, icosapentaenoic acid, docosahexaenoic acid, capric acid, lauric acid, γ-linolenic acid, and arachidonic acid.

Examples of salts of the above-listed fatty acids include sodium salts and potassium salts. Fatty acids that are not soluble enough in water can be dissolved in an organic solvent such as ethanol and then subjected to the production of microparticles.

For example, the microparticles contain sodium oleate or sodium laurate as an anionic surfactant.

[Other Additive]

The microparticles of one embodiment may further contain some other additive(s). Examples of the additive that can be contained include: trehalose, glucose, sucrose, lactose, glucose, mannitol, dextran, xylitol, maltose, fructose, glycine, citric acid, and sodium chloride; and nonionic surfactants. Such additives make it possible to prevent the instability of properties such as agglomeration or a decrease in immunostimulatory activity that would result from freeze drying or long-term preservation at low temperature. Other examples of the additive include vitamin C and vitamin E. Such vitamins make it possible to suppress the oxidative decomposition of the fatty acid.

[Other Component]

The microparticles in another embodiment may have a medicament supported on the surfaces thereof. Alternatively, the surfaces of the microparticles may be coated with an anionic polymer such as a polycarboxylic acid. Examples of the polycarboxylic acid include pectin, alginic acid, polyacrylic acid, hyaluronic acid, chondroitin sulfate, and poly-γ-glutamic acid. The microparticles coated with such a substance are provided with high stability to digestive enzymes.

<Characteristics of Microparticles>

[Zeta Potential]

Generally, particles dispersed in a liquid are positively or negatively charged in many cases, and it is inferred that a layer where oppositely-charged ions are strongly attracted and fixed to the particle surface (such a layer is stationary layer) and a layer outside the stationary layer (such a layer is dispersion layer) forms a so-called diffuse electric double layer, and that an inner portion of the dispersion layer and the stationary layer move along with the particle.

Zeta potential is the electric potential at a plane (slipping plane) where the above-mentioned movement occurs, relative to the electric potential of an electrically neutral region sufficiently far away from the particle. Zeta potential can be used as an indicator of the dispersion state of microparticles. A larger absolute value of zeta potential results in increased repulsion between particles, resulting in increased stability of particles. On the other hand, an absolute value of zeta potential closer to zero results in higher likeliness that particles agglomerate. It is preferred if microparticles are charged such that their surfaces have a positive zeta potential, also for enhancing the adhesiveness of microparticles to negatively charged cell walls to improve the cell-entry ability of bioactive molecules.

In one embodiment, the zeta potential of microparticles is 10 mV to 100 mV, more preferably 20 mV to 50 mV.

(Method of Producing Microparticles)

A method of producing microparticles of the present invention, in one embodiment, includes a step of mixing a [chitosan and/or chitosan derivative] with an anionic surfactant in a solvent.

It appears that microparticles form through: (1) complexing of chitosan and the anionic surfactant via an electrostatic interaction between a protonated amino group ($-NH_3^+$) of chitosan and a deprotonated carboxylate ion ($-COO^-$) formed through deprotonation of a carboxyl group of the anionic surfactant; and (2) association of the anionic surfactant resulting from a hydrophobic interaction (reference document: Takashi Kuroiwa, Urakami-zaidan study report, Vol 22, pp. 16-20 (2005)).

The components of the microparticles are mixed together preferably under the condition in which the pH is neutral to slightly acidic where chitosan becomes cationic.

<Solvent>

The solvent for use in the production of the microparticles may be any solvent that is known to dissolve chitosan. Examples of the solvent include aqueous acetate buffer solutions, aqueous acetic acid solutions, aqueous formic acid solutions, aqueous propionic acid solutions, aqueous malic acid solutions, aqueous succinic acid solutions, and aqueous lactic acid solutions. A buffer is, for example, an acetate buffer at a final concentration of 5 to 50 mM (pH5.0, in physiological saline).

The microparticles can be produced by mixing a [chitosan and/or chitosan derivative] with an anionic surfactant in the above solvent.

The [chitosan and/or chitosan derivative] and the anionic surfactant may be mixed into the solvent in any order. Furthermore, an antigen, the [chitosan and/or chitosan derivative], and the anionic surfactant may be mixed into the solvent in any order, and may be mixed into the solvent concurrently, as will be described later in the Pharmaceutical composition section.

Specifically, assume that an immunostimulator in particulate form of the present invention is provided as a product. In this case, if the immunostimulator product is in the form of a mixture of a [chitosan and/or chitosan derivative] and an anionic surfactant, a user of the product can use the product only by adding a desired antigen to the mixture, and no complicated operations such as mixing two or more components are necessary. Thus, it is possible to provide a product that can be used in a simpler manner.

<Molar Proportions of Components>

The ratio of the [chitosan or chitosan derivative] to the anionic surfactant, per particle of the microparticles, varies depending on the conditions such as the molecular weight of chitosan or the type of surfactant used. In one embodiment, the molar ratio of the amino groups of the [chitosan and/or chitosan derivative] to the anionic groups of the anionic surfactant, per particle of the microparticles, is preferably in the range of from 1:0.05 to 1:1, more preferably from 1:0.1 to 1:0.5, even more preferably from 1:0.15 to 1:0.3.

(Amounts of Components)

The amounts of the [chitosan and/or chitosan derivative] and the anionic surfactant contained in the microparticles are determined by, for example, determining the final concentration of the [chitosan and/or chitosan derivative] in the solvent. For example, a solution is prepared so that the final concentration of the [chitosan and/or chitosan derivative] in a solvent will be 0.1%.

As such, the microparticles in accordance with the present invention can be produced by mixing all components together in an aqueous solvent. This does not necessitate emulsifying operations or the like operations, and thus the microparticles can be produced easily.

[Particle Size]

In cases where an immunostimulator of the present invention is in particulate form for administration into the living body, the size of the particles (particle size) can be, for example, 20 nm to 10 μm.

As used herein, the term "particle size" refers to mean particle size, unless otherwise noted. The term "mean particle size" refers to the mean of the sizes of multiple particles (e.g., 100 particles).

The microparticles of the present invention can be used not only as an adjuvant but also as a drug delivery carrier. Since the microparticles are composed of a [chitosan and/or chitosan derivative] which is biodegradable and harmless to the living body, the microparticles are released in a well-controlled manner in the living body, do not remain in the living body for long time, and completely decompose and disappear over a moderate period of time. As such, the microparticles do not remain within the living body or adversely affect the health of the living body, and thus can be used safely.

Meanwhile, Freund's adjuvant, which has conventionally been used, is seen as a problem from the animal protection point of view, because Freund's adjuvant causes an inflammation and death of tissue at the administration site of a host animal. To address this, the use of Freund's adjuvant is limited by various guidelines (ARAC. Guidelines for the Use of Adjuvants in Research, Revised Apr. 10, 2013 [http://oacu.od.nih.gov/ARAC/documents/Adjuvants.pdf], Canadian Council on Animal Care guidelines on: antibody production (2002) [http://www.ccac.ca/Documents/Standards/Guidelines/Ant ibody_production.pdf]).

In contrast, the immunostimulator of the present invention can be administered without inflicting a severe pain on animals, and can be produced safely, less costly, and easily. Thus, the immunostimulator of the present invention offers a very high level of commercial value.

For example, a conventional micronized chitosan, which is obtained using sodium tripolyphosphate, is being considered to be used as an adjuvant and as a carrier for a medicament that contains a protein, a nucleic acid, or the like. This utilizes ionic bonding between a positively-charged micronized chitosan and a substance with a negatively-charged surface.

In contrast, in the microparticles in accordance with the present invention, a hydrophobic-group-containing substance is used as an anionic surfactant. Therefore, the particles as an adjuvant and an antigen as a substance supported on the particles are bound together not only via ionic bonding but also via hydrophobic bonding. This firmly binds the adjuvant and the antigen together. As such, the microparticles of the present invention can have a dramatically improved level of immunostimulatory activity as compared to conventionally known microparticles. Note that the immunostimulating effect of the immunostimulator of the present invention can be evaluated by determining antibody titer by a known method such as ELISA.

[3. Pharmaceutical Composition]

The following description will discuss a pharmaceutical composition in accordance with the present invention. The present invention provides a pharmaceutical composition that contains, as an active ingredient, an immunostimulator in accordance with the present invention. In one embodiment, the pharmaceutical composition in accordance with the present invention is a composition for activating the immunity of the living body, and an object thereof is to prophylactically and/or therapeutically treat a disease, illness, or disorder by enhancing or improving the immunostimulatory effect.

(Pharmaceutical Composition that Contains Chitosan-Derivative-Containing Immunostimulator)

In one embodiment, the pharmaceutical composition can contain two or more kinds of chitosan derivative in accordance with the present invention in combination. In another embodiment, the pharmaceutical composition further contains at least one antigen. For example, the pharmaceutical composition of the present invention is a vaccination composition. In a further embodiment, the pharmaceutical composition of the present invention further contains at least one selected from suitable solvents, vehicles, excipients, adjuncts, and the like. Examples of the adjuncts to the immunostimulator include wetting agents, emulsifying agents, pH adjustors, and other adjuvants. The following description will discuss constituent components of the pharmaceutical composition.

[Chitosan Derivative]

Any of the chitosan derivatives described in the foregoing [1. Chitosan derivative] section can be suitably used as the chitosan derivative in accordance with the present invention contained in the pharmaceutical composition in accordance with the present invention.

[Antigen]

Examples of the antigen in the pharmaceutical composition of the present invention include antigens such as polypeptide-containing antigens, recombinant proteins, naturally occurring proteins, nucleic acids, and partially degraded versions thereof. The antigen can be derived from, for example, a virus such as HIV virus, a pathogenic organism such as a bacterium, fungus, or parasite, or allergen. The pharmaceutical composition of the present invention, which contains the immunostimulator and the antigen, can be used as a vaccination composition. Furthermore, a pharmaceutical composition which contains a specific antigen can serve as a vaccination composition that is intended to prophylactically and/or therapeutically treat a specific disease, illness, or disorder.

[Solvent]

Examples of the solvent for the pharmaceutical composition of the present invention include water and buffers. Examples of the buffers include physiological saline, phosphate buffer, and Ringer solution. The solvent for use in the composition may be a mixture of two or more of the above listed solvents.

[pH Adjustor]

The pharmaceutical composition in accordance with the present invention may contain at least one pH adjustor. A substance for use in adjusting the pH of the pharmaceutical composition containing the chitosan derivative in accordance with the present invention can either be an alkaline material or an acidic material, depending on need. The alkaline material for use in adjusting pH is, for example, sodium hydroxide or the like. The acidic material for use in adjusting pH is, for example, acetic acid, hydrochloric acid, or the like.

[Other Adjuvant]

In another embodiment, the pharmaceutical composition in accordance with the present invention may contain one or more other adjuvants. Examples of such other adjuvants include alum adjuvant, Freund's complete adjuvant, Freund's incomplete adjuvant, oil adjuvant, saponin, cell wall skeleton constituents, lipopolysaccharides, endotoxin, ablysin, liposome, bacterial DNA, synthetic oligonucleotides, vitamin E, glycolipids, and squalene. In some cases, a combined use of two or more adjuvants provides a synergistic effect in, for example, accelerating immune response, as compared to cases where each adjuvant is used alone.

[Chitosan Derivative Content]

The chitosan derivative content of the pharmaceutical composition of the present invention is preferably 0.01 wt. % to 10 wt. % relative to the total weight of the composition, more preferably 0.1 wt. % to 5 wt. % relative to the total weight of the composition, particularly preferably 0.5 wt. % to 2 wt. % relative to the total weight of the composition. When the chitosan derivative is contained at a concentration equal to or greater than 0.5 wt. %, the chitosan derivative provides a sufficient effect of accelerating immune response reaction. When the chitosan derivative is contained at a concentration equal to or less than 2 wt. %, the viscosity of the composition can be maintained such that the composition is easily workable, for example, maintained at a level that is suitable for a composition for injection.

The viscosity of the pharmaceutical composition of the present invention is preferably equal to or less than 100 mPa·s, more preferably equal to or less than 10 mPa·s. The viscosity can be determined by any method known in the field of the art.

[Dosage Form]

There is no particular limitation on dosage form of the pharmaceutical composition of the present invention, and the dosage form can be liquid, solid, semisolid, or semiliquid. The pharmaceutical composition in such a dosage form can be produced easily based on any method known to those skilled in the art. In cases where the dosage form is liquid, the pharmaceutical composition is, for example, a chitosan-derivative-containing formulation obtained by dispersing, suspending, or dissolving a chitosan derivative in a substantially aqueous solvent. As used herein, the term "substantially aqueous formulation or preparation" in an embodiment is intended to mean a formulation or preparation containing one or more nonaqueous components or one or more other pharmaceutically acceptable components in a certain proportion. In cases where the dosage form is solid, the pharmaceutical composition is, for example, powder, granules, tablet, capsule, or the like. In cases where the dosage form is semisolid or semiliquid, the pharmaceutical composition is, for example, ointment, lotion, cream, gel, or the like.

[Route of Administration]

Examples of the route of administration of the pharmaceutical composition include, but are not limited to, oral, topical, subcutaneous, intramuscular, intravenous, intradermal, transmucosal, and transdermal administrations.

[Way of Administration]

The pharmaceutical composition of the present invention is administered to a subject based on a known method, such as being administered by directly injecting subcutaneously, intradermally, intravenously, intramuscularly, intraperitoneally, or the like, by spraying to an intranasal, intraoral, intrapulmonary, intravaginal, or intrarectal mucous membrane or the like, or being orally administered or intravascularly administered.

[Use Application]

A more specific use application of the pharmaceutical composition of the present invention is, for example, therapeutic or prophylactic treatment of an illness such as cancer, infection, autoimmune disease, or allergy. Examples of the therapeutic or prophylactic treatment include vaccine therapy, immunotherapy for cancer or the like, desensitization therapy for allergenic substances, and the like.

[Subject who Receives Administration]

Examples of a subject who receives administration of the pharmaceutical composition in accordance with the present invention include all kinds of animals. The subject is preferably a vertebrate such as a mammal or a bird, more preferably a mammal. The mammal subject is preferably a human, but can be a domestic animal, a laboratory animal, or a pet animal in some cases. Specific examples of a subject include: domestic animals such as chickens, pigs, horses, goats, sheep, and cattle; pet animals such as cats, dogs, hamsters, rabbits, and guinea pigs; mice; rats; monkeys; fish; and birds.

(Pharmaceutical Composition that Contains Immunostimulator in Particulate Form)

[Antigen]

In another embodiment, the pharmaceutical composition of the present invention contains an immunostimulator in particulate form and an antigen. The immunostimulator in particulate form has already been described in the foregoing [Immunostimulator in particulate form] section. The amount of the antigen contained in the pharmaceutical composition in which the immunostimulator is in particulate form can be selected appropriately depending on the use or administration site.

With the pharmaceutical composition of the present invention, it is possible to achieve a much higher level of immunostimulatory activity and higher neutralizing antibody titer than conventional adjuvants, even with the use of smaller amounts of immunostimulator and antigen. Since the adjuvant and the antigen are contained in smaller amounts, the resulting vaccination composition does not inflict intense stimulations to the living body, is highly safe, and is also less costly.

(Method of Producing Pharmaceutical Composition that Contains Antigen and Microparticles)

A pharmaceutical composition that contains an antigen and microparticles, in one embodiment, can be produced by mixing the antigen, a [chitosan and/or chitosan derivative], and an anionic surfactant in a solvent.

In so doing, the antigen, the [chitosan and/or chitosan derivative], and the anionic surfactant can be mixed into the solvent in any order, and may be mixed into the solvent concurrently. In one example, a [chitosan and/or chitosan derivative] and an antigen are mixed together in a solvent such as a buffer to obtain a mixture, and then an anionic surfactant is added to the mixture. In another example, an anionic surfactant and an antigen are mixed together in a solvent to obtain a mixture, and then a [chitosan and/or chitosan derivative] is added to the mixture. In a further example, a [chitosan and/or chitosan derivative] and an anionic surfactant are mixed together in a solvent to obtain a mixture, and then an antigen is added to the mixture.

[Dosage Form]

Examples of the dosage form are the same as those of the pharmaceutical composition that contains a chitosan-derivative-containing immunostimulator.

[Route of Administration]

Examples of the route of administration of the pharmaceutical composition include, but are not limited to, oral, topical, subcutaneous, intramuscular, intravenous, intradermal, transmucosal, and transdermal administrations. The route of administration of the pharmaceutical composition in which the immunostimulator of the present invention is in particulate form is, for example, oral, subcutaneous, intramuscular, intradermal, transmucosal, or transdermal administration.

[Way of Administration]

The pharmaceutical composition in which the immunostimulator of the present invention is in particulate form is, for example, directly injected intramuscularly, intradermally, or intraperitoneally. Alternatively, the pharmaceutical composition is sprayed to an intranasal, intraoral, intrapulmonary, intravaginal, or intrarectal mucous membrane, or the like. In another embodiment, the pharmaceutical composition in which the immunostimulator of the present invention is in particulate form is orally administered. In cases of oral administration, the microparticles are stable in gastrointestinal fluid and, without being degraded, reach the bowels where the antigen and the like contained in the composition are released.

[Dosage Amount]

The pharmaceutical composition of the present invention is generally administered to a subject such as an animal or a human in an amount that is sufficient to enhance immune system. For example, in a case where the pharmaceutical composition is administered orally to a human, the dosage of the pharmaceutical composition of the present invention can be selected appropriately by a medical doctor in consideration of the patient's condition. In one embodiment, in cases where the foregoing pharmaceutical composition that contains an immunostimulator in particulate form and an antigen is administered to a subject, the dosage amount may be selected appropriately depending on the kind of subject, purpose of administration, frequency of administration, and the like.

The administration in such a dosage amount makes it possible to achieve a sufficient level of immunostimulatory activity while ensuring safety to the living body, without involving adverse effects that would be caused by excessive stimulation of immunity in the subject, and thus is effective.

[Use Application and Subject who Receives Administration]

Examples of the use application and subject who receives administration are the same as those described in the [Pharmaceutical composition that contains chitosan-derivative-containing immunostimulator] section.

[4. Alimentary Product]

The present invention also provides an alimentary product that contains an immunostimulator in accordance with the present invention. In one embodiment, the alimentary product of the present invention contains any of the chitosan derivatives described in the foregoing [1. Chitosan derivative] section. In another embodiment, the alimentary product of the present invention contains, as an active ingredient, an effective amount of any of the immunostimulators described in the foregoing [2. Immunostimulator] section so as to stimulate immune activity of a living body who takes in the alimentary product.

The alimentary product in accordance with the present invention is intended to stimulate immune activity via eating and/or drinking. As used herein, the meaning of the term "alimentary product" not only includes beverages, food, and health foods that humans take in but also includes livestock food and feed given to animals such as domestic animals and pet animals.

The alimentary product is not limited to a particular form, and can be in the form of, for example, a formulation, processed food, or a beverage. Examples of the alimentary product in the form of a formulation include health foods, functional foods, and foods for specified health uses. In cases where the "alimentary product" of the present invention is in the form of a formulation, the alimentary product can be arranged in the same manner as a pharmaceutical composition. That is, the alimentary product for immunostimulation can be such that: the immunostimulator content of the alimentary product is selected in the same manner as the pharmaceutical composition; and the dosage form of the alimentary product is selected in the same manner as the pharmaceutical composition, e.g., a tablet, capsule, drinkable preparation, powder, or the like. In cases where the alimentary product is a processed food, such an alimentary product may be obtained by adding an effective amount of an immunostimulator to a known processed food. Examples of the processed food include breads, noodles, confectionery, and livestock foods. In cases where the alimentary product is a beverage, such an alimentary product may be obtained by adding an effective amount of an immunostimulator to a known beverage. Examples of the beverage include juice, milk beverages, and syrup. A subject, by orally taking the aliment of the present invention, is capable of stimulating the immune system and preventing or improving a disease, illness, or disorder. As such, the immunostimulator in accordance with the present invention may be given to the living body on a long-term basis as a health food or a medical product.

It is inferred that the immunostimulatory effect of a chitosan derivative, an immunostimulator containing the chitosan derivative, a pharmaceutical composition containing the immunostimulator, and an aliment containing the chitosan derivative, in accordance with the present invention, is induced by trapping of an antigen via ionization, micronization caused by addition of complementary anion, retention due to gelation resulting from the pH in the living body, and degradation by lysozyme or phagocyte. The chitosan derivative of the present invention can be arranged to have a variety of desired characteristics to suit the use application, by changing the structure, length, molecular weight, degree of substitution, and/or the like of the main and/or side chains. For example, the chitosan derivative can be arranged to have an appropriate particle size to be delivered into the living body, and can be micronized depending on need by making it into liposomes or the like. This chitosan derivative in accordance with the present invention has been found in the present invention for the first time ever, and is promising for use in various applications.

As such, the chitosan derivative of the present invention is promising not only for use in basic applications such as cosmetics, pharmaceuticals, and materials for medical purposes including dressing materials for medical use, for which conventionally known chitosan and its derivatives have been used, but also for use in new applications such as drug delivery system (DDS) carriers and microcapsules.

Furthermore, the immunostimulator in particulate form of the present invention, despite its high level of safety to the living body and its ability to be produced easily, has a much higher level of immunostimulating effect than conventional Freund's adjuvant and the like. Thus, the immunostimulator in particulate form is suitable for use as an immunologic adjuvant in a vaccination composition and the like.

[5. Examples of Specific Aspects in Accordance with the Present Invention]

For example, the present invention encompasses any of the following subject matters.

<1> An immunostimulator containing: chitosan and/or a chitosan derivative each having a weight-average molecular weight of 10 k to 1000 k; and an anionic surfactant, the immunostimulator being in particulate form.

<2> The immunostimulator according to <1>, wherein the anionic surfactant is at least one selected from the group consisting of phospholipids, C10-C22 fatty acids, and salts of the C10-C22 fatty acids.

<3> The immunostimulator according to <2>, wherein: the phospholipids are selected from the group consisting of lecithin and lysolecithin; and the C10-C22 fatty acids and the salts of the C10-C22 fatty acids are selected from the group consisting of sodium oleate and sodium laurate.

<4> The immunostimulator according to any one of <1> through <3>, wherein the chitosan derivative has immunostimulatory activity and is represented by General Formula (I) below:

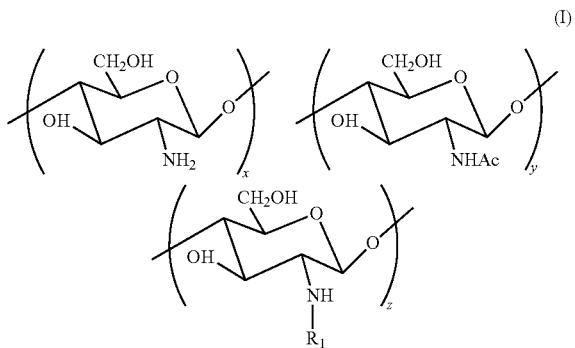

where x, y, and z represent respective molar proportions which satisfy the equation $x+y+z=1$, where $0 \leq x < 1$, $0 \leq y < 1$, and $0 < z \leq 1$, the number of saccharide units falls within the range of from 30 to 12,000, and $R^1$ is a pullulan side chain represented by General Formula (II) below:

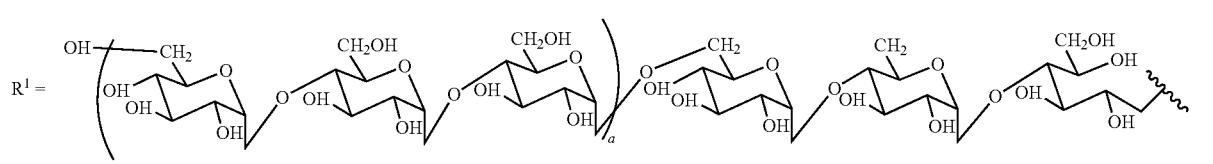

wherein a represents an integer of 20 to 600, a degree of substitution with the pullulan side chain being 0.001 to 0.1, a dextran side chain represented by General Formula (III) below:

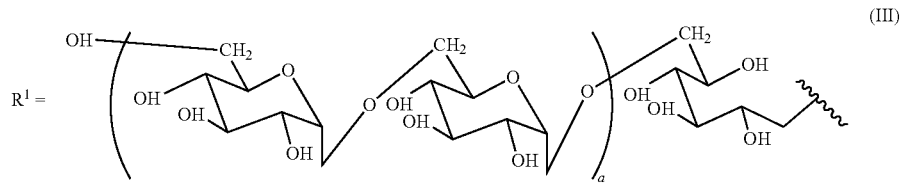

where a represents an integer of 15 to 300, a degree of substitution with the dextran side chain being 0.001 to 0.1, a glucosamine side chain represented by General Formula (IV) below:

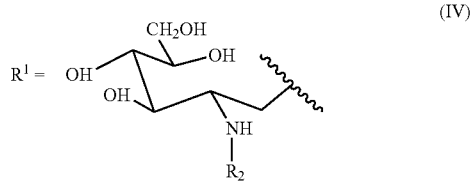

where $R^2$ represents an acetyl group, a degree of substitution with the glucosamine side chain being 0.05 to 0.5, or a lysine side chain represented by General Formula (V) below:

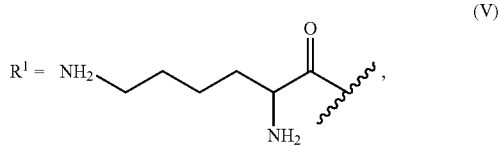

a degree of substitution with the lysine side chain being 0.02 to 0.5.

<5> The immunostimulator according to <4>, wherein the number of the saccharide units in General Formula (I) falls within the range of from 60 to 6,000.

<6> The immunostimulator according to <4> or <5>, wherein z in General Formula (I) is 0.001 to 0.5.

<7> The immunostimulator according to any one of <1> through <6>, wherein a molar ratio of (i) amino groups of the chitosan and/or the chitosan derivative to (ii) anionic groups of the anionic surfactant, per particle of the immunostimulator in particulate form, is 1:0.05 to 1:1.

<8> A pharmaceutical composition containing, as an active ingredient, an immunostimulator as set forth in any one of <1> through <7>.

<9> An alimentary product containing an immunostimulator as set forth in any one of <1> through <7>.

The present invention is not limited to the embodiments, but can be altered by a skilled person in the art within the scope of the claims. The present invention also encompasses, in its technical scope, any embodiment derived by combining technical means disclosed in differing embodiments. Further, it is possible to form a new technical feature by combining the technical means disclosed in the respective embodiments.

EXAMPLES

Example 1: Synthesis of Chitosan Derivative (Synthesis of Ch10-Dex)

Chitosan 10 (1.00 g, amino group 5.08 mmol) (available from Wako Pure Chemical Industries Ltd., degree of deacetylation 85%, Lot TLE3201) was dispersed in water (45 mL), acetic acid (300 μL) was added and thereby chitosan 10 was dissolved, and then dextran 40 (4.00 g) (available from Meito Sangyo Co., Ltd., weight-average molecular weight Mw 40,000, Lot CL-A594A) was further added and dissolved. Then, 2-picoline borane (100 mg, 0.93 mmol) was added and stirred for 25 hours. The resulting mixture was freeze-dried after ultrafiltration, and thereby a chitosan derivative with dextran side chain (dextran-branch chitosan) Ch10-Dex (2.33 g) was obtained.

$^1$H-NMR (400 MHz, D$_2$O+TFA-d): δ 2.07 (CH$_3$ of NHCOCH$_3$), 3.19 (H at C2 of GlcN), 3.50-4.00 (H at C2, C3, C4, C5, C6 of other saccharide residues)

A comparison in terms of spectrum between Ch10-Dex and chitosan 10 (source material) showed that the dextran content of Ch10-Dex is 69%. Assuming here that the molecular weight of chitosan is about 100,000, the number of glucosamine units constituting chitosan is 600 residues and thus the ratio of the number of chitosan molecules to the number of dextran molecules is 1:5.6. It follows that 5.6 substituted residues/600 residues=a degree of substitution of 0.01. Furthermore, the number of disaccharide units constituting dextran, calculated using the equation: Number of disaccharide units constituting dextran=Dextran's average molecular weight 40,000/Disaccharide unit's molecular weight 324, was found to be about 120.

(Synthesis of Ch10-Pul)

Chitosan 10 (500 mg, amino group 2.54 mmol) (available from Wako Pure Chemical Industries Ltd., degree of deacetylation 85%, Lot TLE3201) was dispersed in water (22.5 mL), acetic acid (150 μL) was added and thereby chitosan 10 was dissolved, and then low-molecular-weight pullulan (2.00 g, reducing end residues 0.071 mmol) (weight-average molecular weight Mw 73,000, number-average molecular weight Mn 28,000) was further added and dissolved. Then, 2-picoline borane (50 mg, 0.47 mmol) was added, and stirred for 24 hours. The resulting mixture was freeze-dried after ultrafiltration, and thereby a pullulan-branch chitosan Ch10-Pul (1.39 g) was obtained. $^1$H-NMR (400 MHz, D$_2$O+TFA-d): δ 2.10 (CH$_3$ of NHCOCH$_3$), 3.20 (H at C2 of GlcN), 3.40-4.10 (H at C2, C3, C4, C5, C6 of other saccharide residues)

A comparison in terms of spectrum between Ch10-Pul and chitosan 10 (source material) showed that the pullulan content of Ch10-Pul is 72%. Assuming here that the molecular weight of chitosan is about 100,000, the number of glucosamine units constituting chitosan is 600 residues and thus the ratio of the number of chitosan molecules to the number of pullulan molecules is 1:3.5. It follows that 3.5 substituted residues/600 residues=a degree of substitution of 0.006. Furthermore, the number of trisaccharide units constituting pullulan, calculated using the equation: Number of trisaccharide units constituting pullulan=Average molecular weight 73,000/Trisaccharide unit's molecular weight 486, was found to be about 150.

(Synthesis of Ch10-GlcNAc)

Chitosan 10 (500 mg, amino group 2.54 mmol) (available from Wako Pure Chemical Industries Ltd., degree of deacetylation 85%, Lot TLE3201) was dispersed in water (20 mL), acetic acid (200 μL) was added and thereby chitosan 10 was dissolved, and then N-acetyl-D-glucosamine (550 mg, 2.48 mmol) was added and dissolved. Then, 2-picoline borane (266 mg, 2.49 mmol) and water were added so that the total amount of the resulting solution would be 25 g, and then stirred for 18 days. The resulting mixture was freeze-dried after ultrafiltration, and thereby N-acetyl-D-glucosamine-branch chitosan Ch10-GlcNAc (642 mg) was obtained.

$^1$H-NMR (400 MHz, D$_2$O+TFA-d): δ 2.10 (CH$_3$ of NHCOCH$_3$), 3.21 (H at C2 of GlcN), 3.32 (H at C2 of substituted GlcN), 3.50-4.40 (H at C2, C3, C4, C5, and C6 of other saccharide residues)

The degree of substitution was found to be 0.26 from the ratio in terms of H at C2 between substituted GlcN groups and unsubstituted GlcN groups.

(Synthesis of Ch10-Lys)

Chitosan 10 (500 mg, amino group 2.54 mmol) (available from Wako Pure Chemical Industries Ltd., degree of deacetylation 85%, Lot TLE3201) was dispersed in water (15 mL), 1M-hydrochloric acid (1.9 mL) was added and thereby chitosan 10 was dissolved, and then a 1M aqueous sodium hydrogencarbonate solution was added to adjust the pH to 6. L-lysine monohydrochloride (696 mg, 3.81 mmol) was added and dissolved, and then 4-(4,6-dimethoxy-1,3,5-triazine-2-yl)-4-methylmorpholinium chloride (1.12 g, 3.81 mmol) and water were added so that the total amount of the resulting solution would be 25 g, and then stirred for 24 hours. The resulting mixture was freeze-dried after ultrafiltration, and thereby L-lysine-branch chitosan Ch10-Lys (506 mg) was obtained.

$^1$H-NMR (400 MHz, D$_2$O+TFA-d): δ 1.52 (lysine γ-CH$_2$), 1.73 (lysine δ-CH$_2$), 1.90 (lysine β-CH$_2$), 2.08 (derived from CH$_3$ of NHCOCH3), 3.00 (lysine ε-CH$_2$), 3.19 (H at C2 of GlcN), 3.40-4.40 (H at C2, C3, C4, C5, and C6 of other saccharide residues)

The degree of substitution was found to be 0.09 from the ratio in terms of H at C2 between lysine and unsubstituted GlcN groups.

(Synthesis of FL80-Dex)

FL-80 (500 mg, amino group 2.72 mmol) (available from KOYO CHEMICAL CO., LTD., degree of deacetylation 90%, weight-average molecular weight Mw 30 k (3,000), Lot 0507-27) was dispersed in water (25 mL), acetic acid (200 μL) was added and thereby FL-80 was dissolved, and then dextran 40 (2.00 g) (available from Meito Sangyo Co., Ltd., weight-average molecular weight Mw 29 k (29,000), Lot CL-A594A) was further added and dissolved. Then, 2-picoline borane (50 mg, 0.47 mmol) was added, and stirred for 24 hours. The resulting mixture was freeze-dried after ultrafiltration, and thereby a chitosan derivative with dextran side chain, FL80-Dex, (876 mg) was obtained.

$^1$H-NMR (400 MHz, D$_2$O+TFA-d): δ 2.07 (CH$_3$ of NHCOCH$_3$), 3.18 (H at C2 of GlcN), 3.50-4.10 (H at C2, C3, C4, C5, and C6 of other saccharide residues), 4.58 (H at C1 of N-acetyl glucosamine), 4.87 (H at C1 of glucosamine), 4.98 (H at C1 of dextran)

A comparison in terms of spectrum between FL80-Dex and FL-80 (source material) showed that the dextran content of FL80-Dex is 50 mol % (mol % of monosaccharides). Assuming here that the molecular weight of chitosan is about 30,000, the number of glucosamine units constituting chitosan is 180 residues and thus the ratio of the number of chitosan molecules to the number of dextran molecules is 1:1.03. It follows that 1.03 substituted residues/180 residues=a degree of substitution of 0.0057.

Example 2: Evaluation Test on Activity of Chitosan Derivative as Antibody Adjuvant Tests were carried out to evaluate the activity of the chitosan derivatives produced in Example 1 as antibody adjuvants, in the following manner.

(Test Materials)

<Tested Animal>

Five-week-old female Balb/c mice were randomly selected into groups such that each group would include three mice, after one week of habituation.

<Immunizing Antigen>

The mice thus grouped into Groups 1 to 6 received administration of the following test solutions, and were used in the following experiments. Physiological saline was used for Group 1 as a control group, nonderivative chitosan (chitosan 10 as a source material used in Example 1) was used for Group 2 as a comparative example, the dextran-branch chitosan prepared in Example 1 was used for Group 3, the pullulan-branch chitosan prepared in Example 1 was used for Group 4, the N-acetyl-glucosamine-branch chitosan prepared in Example 1 was used for Group 5, and the lysine-branch chitosan prepared in Example 1 was used for Group 6. Each of the chitosan and chitosan derivatives for Groups 2 to 6 was dissolved at a concentration of 2% in 10 mM acetate buffer (pH5.0), and an aliquot of 500 μL was taken. In regard to Group 1, 500 μL of physiological saline was used because Group 1 was a control group. To the solution of each group, a 4 μg/mL antigen solution (peptide conjugate KLH: Sigma-Aldrich, solvent: physiological saline) in an amount equal to the solution was added to obtain a mixture. The mixture was used as an immunizing antigen. The immunizing dose per mouse was 100 μL.

(Test Method)

<Immunization Schedule>

Each mouse received the first immunization (intraperitoneal administration) when it was six weeks old, and then received booster immunizations in the same manner at 2-week intervals. Blood was collected from tail vein one week after every booster immunization, and blood serum was obtained.

<Method of Determining Antibody Titer>

Procedures of Blood Serum Dilution

The blood serum thus obtained was 100-fold diluted with a diluent (0.1% BSA, 0.025% Tween-20 PBS [phosphate buffered saline]), and the resultant solution was used as a stock sample. The stock sample was 10-fold diluted to obtain a 1000-fold diluted solution, and then was 3-fold serially diluted until a 2187000-fold diluted solution was obtained. In this way, diluted solutions with stepwise increasing dilution degrees were prepared.

Preparation of Evaluation Plate

Keyhole limpet hemocyanin (KLH) was dissolved at a concentration of 2 µg/mL in a carbonate buffer, and dispensed in aliquots of 50 µL into a 96-well titer plate to prepare a solid phase plate for each antigen. The solid phase plate was used as an evaluation plate.

Determination of Antibody Titer

To the wells in each column of the evaluation plate, the diluted blood serum solutions with stepwise increasing dilution degrees (1000-fold to 2187000-fold diluted solutions) from one of the foregoing mice were dispensed in aliquots of 50 µL, and allowed to undergo an antigen-antibody reaction at 4° C. overnight. Then, the plate was washed three times with 100 µL of a rinse solution (T-PBS), and POD-labeled anti-mouse IgG (Simple Stain MAX-PO (M): NICHIREI/100-fold diluted) or POD-labeled anti-mouse IgM (Sigma-Aldrich/10000-fold diluted) was used as a secondary antibody to allow a further reaction to take place. After one hour of the reaction, washing was carried out, color development was allowed for 10 minutes at room temperature using a TMB substrate, and the reaction was terminated with 2N sulfuric acid. Immediately after the termination of the reaction, the absorbance was determined with a plate reader (reading wavelength: 450 nm, reference wavelength: 650 nm). The antibody titers of IgM against KLH thus obtained are shown in FIG. 1. FIG. 1 shows the antibody titers after the administration of the chitosan derivatives. In FIG. 1, the antibody titers for Groups 1 to 6 after the second immunization and those after the third immunization are shown for (a) cases where blood serum is 1000-fold diluted and (b) cases where blood serum is 3000-fold diluted.

Example 3: Titer Increase Resulting from Micronization

Each of the following groups was evaluated for titer of antigen-specific antibody after the second immunization of mice.

(Test Materials)

<Tested Animal>

In the same manner as described in Example 2, five-week-old female Balb/c mice were randomly selected into groups such that each group would include three mice, after one week of habituation.

<Immunizing Antigen>

The mice thus grouped into Groups 1 to 5 received administration of the following test solutions, and were used in the following experiments. Freund's adjuvant was used for Group 1 as a comparative example, nonderivative chitosan (FL80 as a source material used in Example 2) was used for Group 2, the dextran-branch chitosan (FL80-Dex) prepared in Example 2 was used for Group 3, nonderivative chitosan (FL80+OA) micronized with sodium oleate was used for Group 4, and the dextran-branch chitosan (FL80-Dex+OA) micronized with sodium oleate (OA) was used for Group 5.

The test solution used for Group 1 was obtained by mixing ovalbumin (OVA) (available from Wako Pure Chemical Industries Ltd., in physiological saline at 20 µg/mL) as an antigen solution and Freund's complete adjuvant (available from Thermo Fisher Scientific) at a ratio of 1:1 and then emulsifying it with the use of two Luer-Lok syringes connected together with a double-hub needle. The amount of administration of the solution was 100 µL per mouse, and the dose of the antigen was 1 µg per mouse. For Groups 2 to 5, the final concentration of chitosan was 0.1%, and the amount of the additive added was 0.28 equivalents of the chitosan's amino group. The buffer used was an acetate buffer (pH5.0, in physiological saline), and the final concentration was 5 mM. The amount of administration of the solution was 100 µL per mouse. Ovalbumin (OVA) (available from Wako Pure Chemical Industries Ltd.) as an antigen solution was mixed into the test solution for each group to obtain a mixture so that the dose of the antigen would be 1 µg per mouse, and this mixture was used as an immunizing antigen.

(Test Method)

<Immunization Schedule>

Each mouse received the first immunization when it was six weeks old, and then received a booster immunization in the same manner two weeks after the first immunization. Blood was collected from tail vein one week after the second immunization, and blood serum was obtained.

<Method of Determining Antibody Titer>

Procedures of Blood Serum Dilution

The blood serum thus obtained was 100-fold diluted with a diluent (0.1% BSA, 0.025% Tween-20 PBS [phosphate buffered saline]), and the resultant solution was used as a stock sample. The stock sample was 10-fold diluted to obtain a 1000-fold diluted solution, and then was 3-fold serially diluted until a 2,187,000-fold diluted solution was obtained. In this way, diluted solutions with stepwise increasing dilution degrees were prepared.

Preparation of Evaluation Plate

OVA was dissolved at a concentration of 2 µg/mL in a carbonate buffer, and dispensed in aliquots of 50 µL into a 96-well titer plate to prepare a solid phase plate for each antigen. The solid phase plate was used as an evaluation plate.

Determination of Antibody Titer

To the wells in each column of the evaluation plate, the diluted blood serum solutions with stepwise increasing dilution degrees (1000-fold to 2187000-fold diluted solutions) from one of the foregoing mice were dispensed in aliquots of 50 µL, and allowed to undergo an antigen-antibody reaction at 4° C. overnight. Then, the plate was washed three times with 100 µL of a rinse solution (T-PBS), and POD-labeled anti-mouse IgG (Simple Stain MAX-PO (M): NICHIREI/100-fold diluted) was used as a secondary antibody to allow a further reaction to take place. After one hour of the reaction, washing was carried out, color development was allowed for 5 minutes at room temperature using a TMB substrate, and the reaction was terminated with 2N sulfuric acid. Immediately after the termination of the reaction, the absorbance was determined with a plate reader (reading wavelength: 450 nm, reference wavelength: 650 nm).

Figure 2:
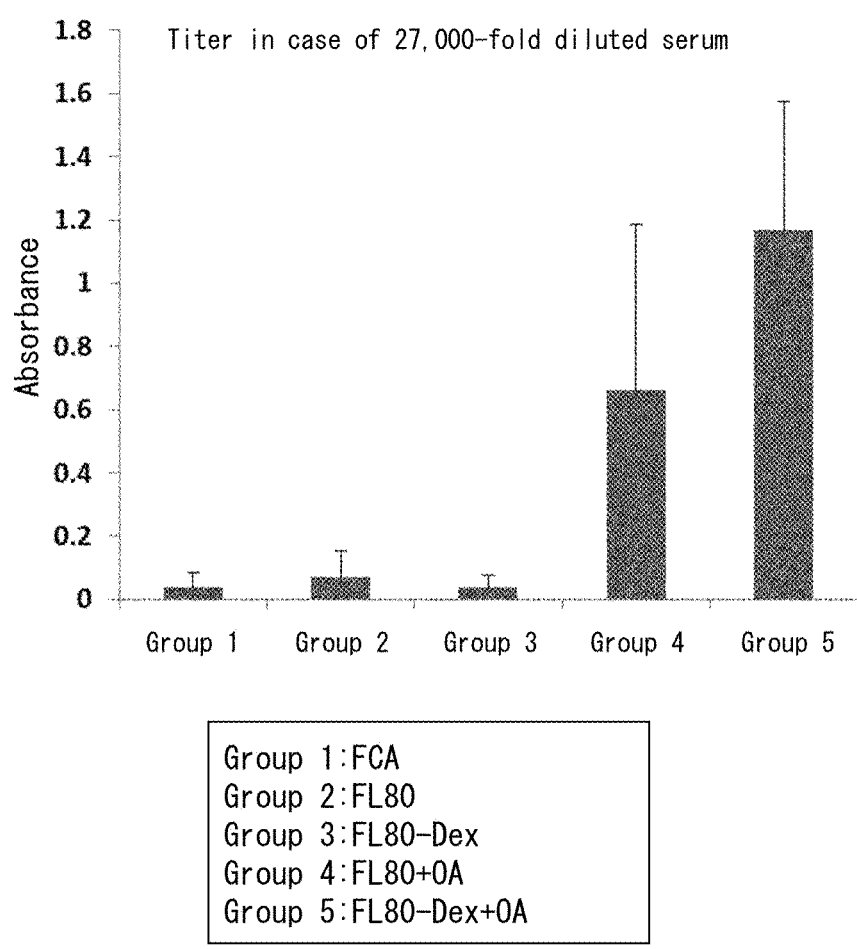
FIG. 2 shows antibody titers after the intraperitoneal administration of chitosan, chitosan derivative, micronized chitosan, and micronized chitosan derivative to mice, in accordance with Example 3 of the present invention.

The antibody titers of IgG against OVA thus obtained are shown in FIG. 2. The results shown in FIG. 2 demonstrate that Groups 4 and 5, in which sodium oleate was added, were 400 times as great in titer as the FCA-administered group.

Example 4: Evaluation of Additive

For study of an additive for use in micronization, each of the following groups was evaluated for titer of antigen-specific antibody after the second immunization of mice.

(Test Materials)
<Tested Animal>
In the same manner as described in Example 2, five-week-old female Balb/c mice were randomly selected into groups such that each group would include three mice, after one week of habituation.
<Immunizing Antigen>
The mice thus grouped into Groups 1 to 8 received administration of the following test solutions, and were used in the following experiments. Freund's adjuvant was used for Group 1 as a comparative example, and dextran-branch chitosans (FL80-Dex) micronized with sodium oleate, with sodium laurate, with lysolecithin, with sodium cholate, with sodium tripolyphosphate, with sodium hyaluronate, and with sodium alginate, respectively, were used for Groups 2 to 8, respectively.

The same antigen solution as that used for Group 1 of Example 3 was used for Group 1. For Groups 2 to 8, the final concentration of chitosan was 0.1%, and the amount of the additive added was 0.28 equivalents of the chitosan's amino group. The buffer used was an acetate buffer (pH5.0, in physiological saline), and the final concentration was 5 mM. The amount of administration of the solution was 100 per mouse. Ovalbumin (OVA) (solvent: physiological saline) as an antigen solution was mixed into the test solution for each group to obtain a mixture so that the dose of the antigen would be 1 μg per mouse, and this mixture was used as an immunizing antigen. The immunization schedule and the method of determining antibody titer were the same as those of Example 3.

Figure 3:
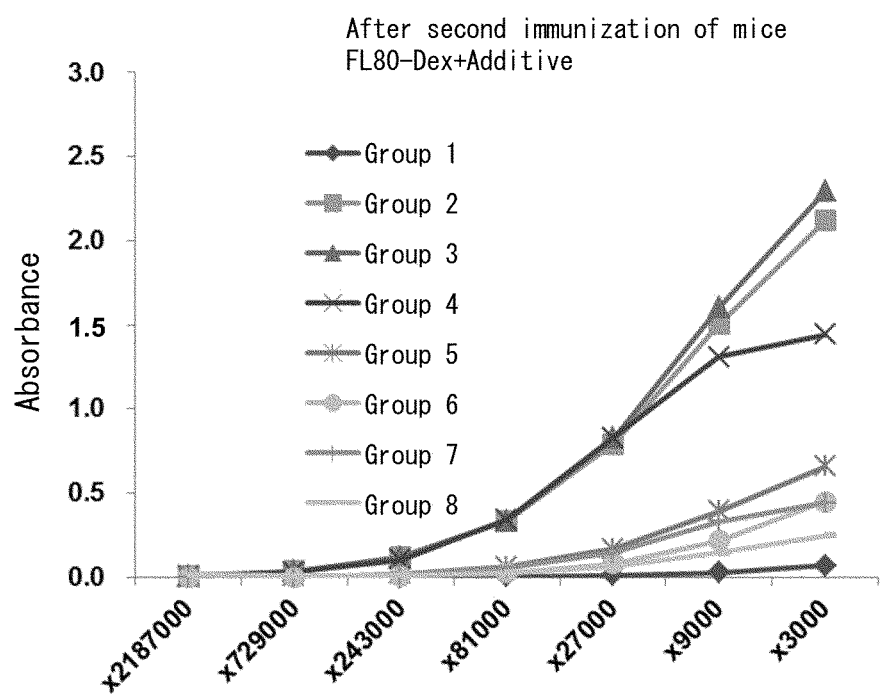
FIG. 3 shows antibody titers after the intraperitoneal administration of micronized chitosan derivatives prepared using different additives to mice, in accordance with Example 4 of the present invention.

The antibody titers of IgG against OVA thus obtained are shown in FIG. 3. In FIG. 3, the horizontal axis shows the dilution degree of each blood serum solution, and the vertical axis shows absorbance. It was found that the absorbance at 3000-fold dilution for the FCA-administered Group 1 (comparative example) and the absorbance at 729000-fold dilution for Groups 2 to 4 were substantially equivalent to each other. This implies that, by the foregoing administrations to the mice of Groups 2 to 4, about 250 times as great an amount of antibody as the FCA-administered mice is produced.

The results shown in FIG. 3 demonstrate that alkyl-chain-containing anionic surfactants, such as sodium oleate used for Group 2, sodium laurate used for Group 3, and lysolecithin used for Group 4, are particularly effective in increasing titer.

Example 5: Evaluation of Fatty Acid Salt

For further study of a fatty acid salt for use in micronization, each of the following groups was evaluated for titer of antigen-specific antibody after the second immunization of mice.
(Test Materials)
<Tested Animal>
In the same manner as described in Example 2, five-week-old female Balb/c mice were randomly selected into groups such that each group would include three mice, after one week of habituation.
<Immunizing Antigen>
The mice thus grouped into Groups 1 to 3 received administration of the following test solutions, and were used in the following experiments. Freund's adjuvant was used for Group 1 as a comparative example, and chitosans (FL80) micronized with sodium laurate and with capric acid, respectively, were used for Groups 2 and 3, respectively.

The same antigen solution as that used for Group 1 of Example 3 was used for Group 1. For Groups 2 and 3, the final concentration of chitosan was 0.1%, and the amount of the additive added was 0.28 equivalents of the chitosan's amino group. The buffer used was an acetate buffer (pH5.0, physiological saline), and the final concentration was 5 mM. The amount of administration of the solution was 100 per mouse. Ovalbumin (OVA) (solvent: physiological saline) as an antigen solution was mixed into the test solution for each group to obtain a mixture so that the dose of the antigen would be 1 μg per mouse, and this mixture was used as an immunizing antigen. The immunization schedule and the method of determining antibody titer were the same as those of Example 3.

Figure 4:
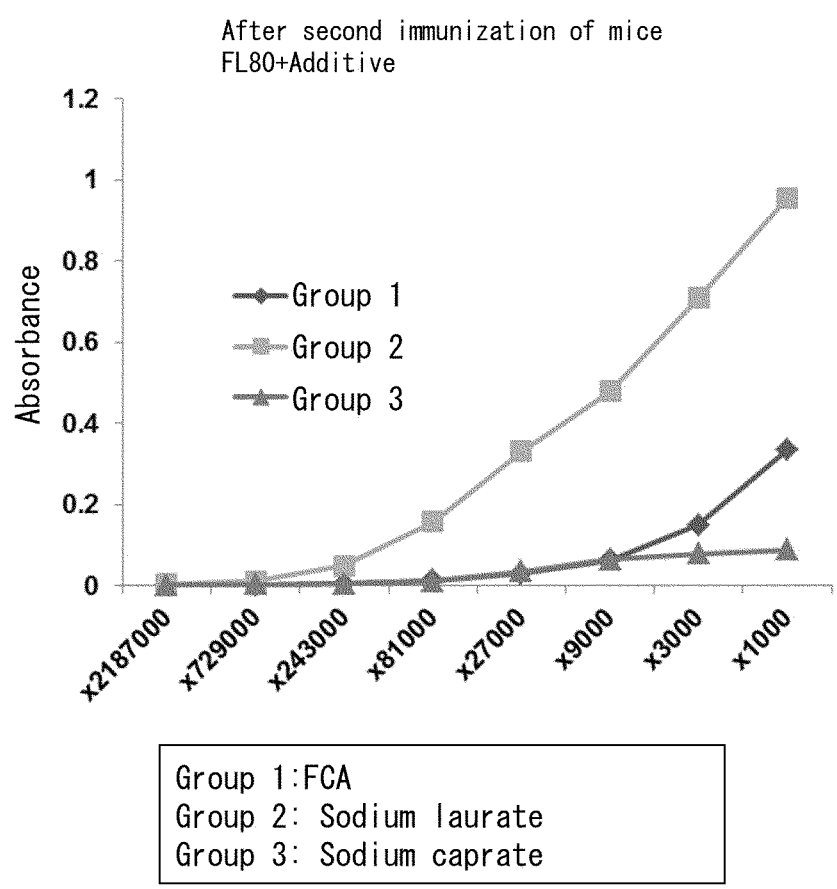
FIG. 4 shows antibody titers after the intraperitoneal administration of micronized chitosan derivatives prepared using different fatty acid salts to mice, in accordance with Example 5 of the present invention.

The antibody titers of IgG against OVA thus obtained are shown in FIG. 4. In FIG. 4, the horizontal axis shows the dilution degree of each blood serum solution, and the vertical axis shows absorbance.

The results shown in FIG. 4 demonstrate that the micronization with sodium laurate in Group 2 is particularly effective in increasing titer.

Example 6: Evaluation of Chitosan's Molecular Weight

For evaluation of the effect of chitosan's molecular weight on antibody titer, each of the following groups was evaluated for titer of antigen-specific antibody after the second immunization of mice.
(Test Materials)
<Tested Animal>
In the same manner as described in Example 2, five-week-old female Balb/c mice were randomly selected into groups such that each group would include three mice, after one week of habituation.
<Immunizing Antigen>
The mice thus grouped into Groups 1 to 7 received administration of the following test solutions, and were used in the following experiments. Ch100 (Mw 1000 k) was used for Group 1, FM-40 (Mw 500 k) was used for Group 2, FM-40 (Mw 410 k) was used for Group 3, Ch10 (Mw 65 k) was used for Group 4, FL-80 (Mw 30 k) was used for Group 5, low-molecular-weight chitosan (Mw 4.1 k) was used for Group 6, and oligoglucosamine (trade name: KOYO Oligo Glucosamine WG (di- to octa-saccharide [Mw 340 to 1306] KOYO CHEMICAL CO., LTD.) was used for Group 7.

Figure 5:
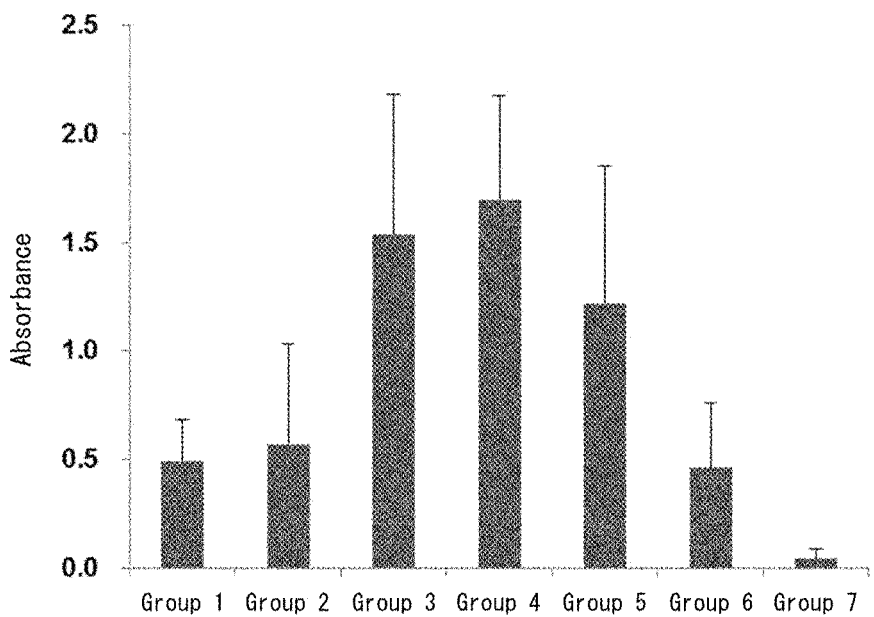
FIG. 5 shows antibody titers after the intraperitoneal administration of microparticles to mice in accordance with Example 6 of the present invention. The microparticles were synthesized using chitosan with different molecular weights in the production of the microparticles.

Ch100 (available from Wako Pure Chemical Industries Ltd., degree of deacetylation 83%, Lot DPH0279), FM-40 (available from KOYO CHEMICAL CO., LTD., degree of deacetylation 92%, Lot 0402-27, and degree of deacetylation 95%, Lot 0930-26), Ch10 (available from Wako Pure Chemical Industries Ltd., degree of deacetylation 85%, Lot TLE3201), and FL-80 (available from KOYO CHEMICAL CO., LTD., degree of deacetylation 90%, Lot 0507-27) for respective Groups 1 to 5 were each dissolved in a 2.5% acetic acid solution and then freeze-dried into an acetic acid salt before use. The low-molecular-weight chitosan for Group 6 was obtained by hydrolyzing FL-80 in 7% hydrochloric acid at 80° C. for 3 hours, carrying out ultrafiltration, and then freeze-drying a 3 k to 10 k fraction. KOYO Oligo Glucosamine WG (available from KOYO CHEMICAL CO., LTD., Lot 140910WG) for Group 7 was used as-is. The amount of the additive (sodium laurate) mixed was 0.28 equivalents of the chitosan's amino group. The buffer used to adjust the total amount of the chitosan derivative and the additive so that the final concentration of them would be 0.1% was an acetate buffer (pH5.0, in physiological saline), and the final concentration of the buffer was 5 mM. The amount of administration of the solution was 100 μL per mouse. Ovalbumin (OVA) as an antigen solution was mixed into the test solution for each group to obtain a mixture so that the dose of the antigen would be 1 μg per mouse, and this mixture was used as an immunizing antigen. The immunization schedule and the method of determining antibody titer were the same as those of Example 3. The antibody titers of IgG against OVA thus obtained are shown in FIG. 5. The results shown in FIG. 5 demonstrate that the use of chitosan having an Mw of 30 k to 500 k provides especially high antibody titers.

Example 7: Evaluation of Chitosan-to-Additive Mixing Ratio

For evaluation of the effect of the chitosan-to-additive mixing ratio on antibody titer, each of the following groups was evaluated for titer of antigen-specific antibody after the second immunization of mice.
(Test Materials)
<Tested Animal>
In the same manner as described in Example 2, five-week-old female Balb/c mice were randomly selected into groups such that each group would include three mice, after one week of habituation.
<Immunizing Antigen>
The mice thus grouped into Groups 1 to 5 received administration of the following test solutions, and were used in the following experiments. For Groups 1 to 3, dextran-branch chitosans (FL80-Dex+OA) micronized with sodium oleate (OA) were used. The mixing ratio between the chitosan derivative and the additive (i.e., the chitosan derivative-to-additive ratio) was 1/0.28 in Group 1, 1/1 in Group 2, and 1/7 in Group 3.

For each group, chitosan derivative FL80-Dex was used, and the amount of the additive (sodium oleate) mixed was 0.28 to 7 equivalents of the chitosan's amino group. The solution for each group was prepared so that the total amount (final concentration) of the chitosan derivative and the additive would be 0.12%. The buffer used was an acetate buffer (pH5.0, in physiological saline), and the final concentration was 5 mM. The amount of administration of the solution was 100 μL per mouse. Ovalbumin (OVA) as an antigen solution was mixed into the test solution for each group to obtain a mixture so that the dose of the antigen would be 1 μg per mouse, and this mixture was used as an immunizing antigen. The immunization schedule and the method of determining antibody titer were the same as those of Example 3. The antibody titers of IgG against OVA thus obtained are shown in FIG. 6.

In addition, for each group having the foregoing chitosan derivative-to-additive mixing ratio, a liquid mixture system containing no antigen was prepared by the same preparation process as that described earlier, except that no antigen was contained, and thereby microparticles were prepared. These microparticles were measured for mean particle size and zeta potential. The mean particle size was measured with the use of a concentrated system particle size analyzer (available from OTSUKA ELECTRONICS Co., LTD., FPAR-1000). The zeta potential was measured with the use of a laser zeta potentiometer (available from OTSUKA ELECTRONICS Co., LTD., ELS-8000). The results of measurement of mean particle size and zeta potential are shown in FIG. 7.

Figure 6:
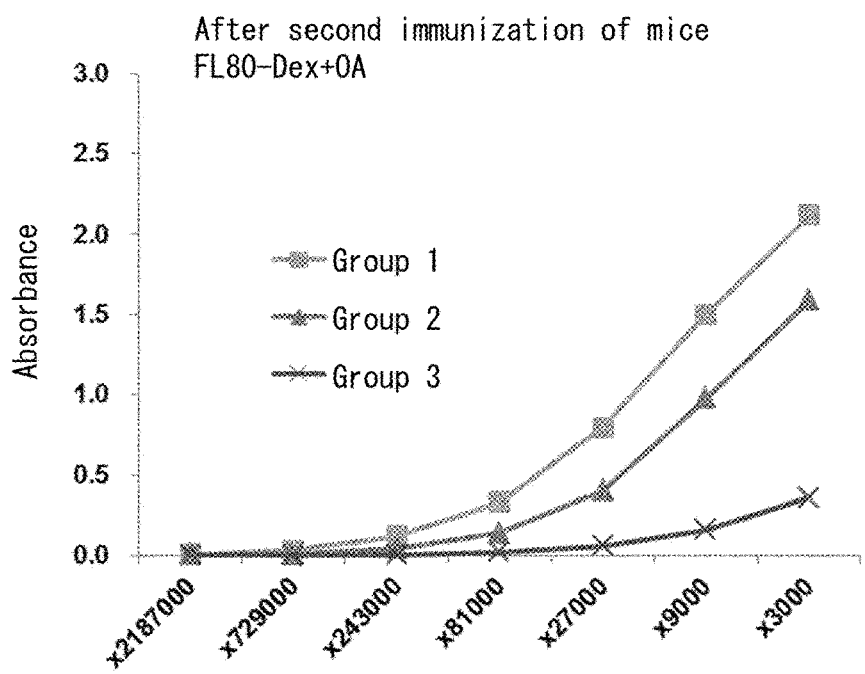
FIG. 6 shows antibody titers after the intraperitoneal administration of microparticles with different chitosan-to-additive mixing ratios to mice, in accordance with Example 7 of the present invention.
Figure 7:
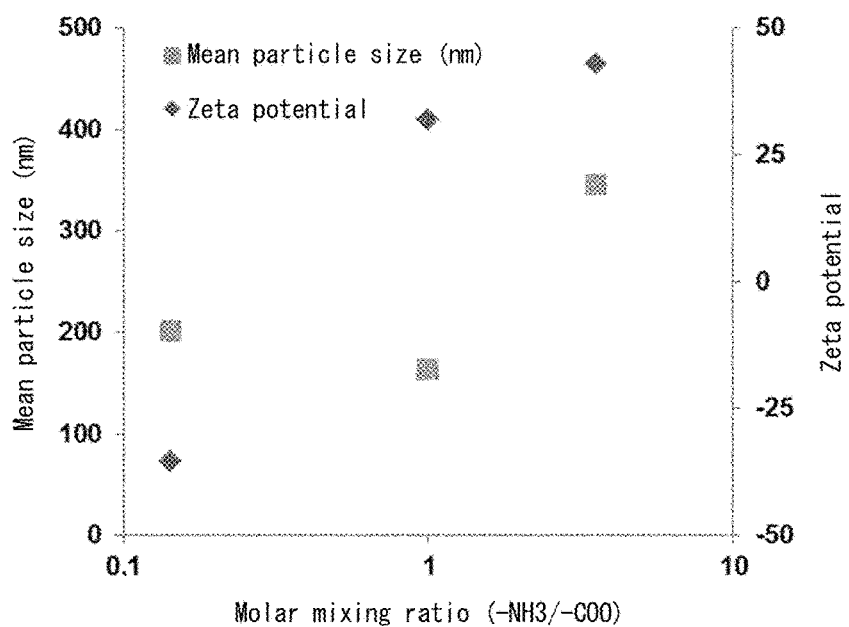
FIG. 7 shows the results of measurement of mean particle size and zeta potential, in accordance with Example 7 of the present invention.

The results shown in FIGS. 6 and 7 demonstrate that Group 3, in which an excessive amount of additive was used, experienced a significant decrease in antibody titer. It is inferred that this decrease in antibody titer is partially because of a change of zeta potential to a negative potential.

Example 8: Evaluation of the Order in which Chitosan Solution, Additive Solution, and Antigen Solution are Mixed For evaluation of what effect the order in which a chitosan solution, an additive solution, and an antigen solution are mixed imposes on antibody titer, each of the following groups was evaluated for titer of antigen-specific antibody after the second immunization of mice.
(Test Materials)
<Tested Animal>
In the same manner as described in Example 2, five-week-old female Balb/c mice were randomly selected into groups such that each group would include three mice, after one week of habituation.
<Immunizing Antigen>
The mice thus grouped into Groups 1 to 5 received administration of the following test solutions, and were used in the following experiments. For Group 1, micronized dextran-branch chitosan (FL80-Dex+OA) was used, which was obtained by mixing chitosan derivative (FL80-Dex) and an antigen (OVA) and then adding sodium oleate (OA) and micronizing the mixture. For Group 2, micronized dextran-branch chitosan (FL80-Dex+OA) was used, which was obtained by mixing sodium oleate (OA) and an antigen (OVA) and then adding chitosan derivative (FL80-Dex) and micronizing the mixture. For Group 3, micronized dextran-branch chitosan (FL80-Dex+OA) was used, which was obtained by mixing chitosan derivative (FL80-Dex) and sodium oleate (OA) and then adding an antigen (OVA) and micronizing the mixture.

Figure 8:
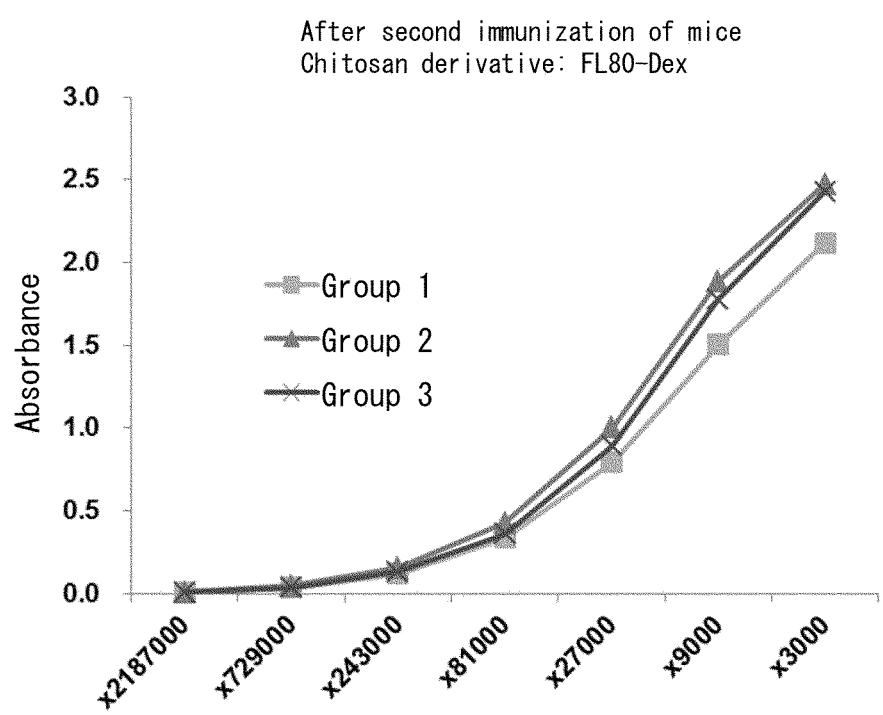
FIG. 8 shows antibody titers after the intraperitoneal administration, to mice, of microparticles produced through processes which are different in the order in which a chitosan derivative solution, an additive solution, and an antigen solution are mixed, in accordance with Example 8 of the present invention.

Chitosan used was FL80-Dex and the final concentration of chitosan was 0.1%, and the amount of the additive mixed was 0.28 equivalents of the chitosan's amino group. The buffer used was an acetate buffer (pH5.0, in physiological saline), and the final concentration was 5 mM. The amount of administration of the solution was 100 per mouse. Ovalbumin (OVA) as an antigen solution was mixed into the test solution for each group to obtain a mixture so that the dose of the antigen would be 1 μg per mouse, and this mixture was used as an immunizing antigen. The immunization schedule and the method of determining antibody titer were the same as those of Example 3. The antibody titers of IgG against OVA thus obtained are shown in FIG. 8. The results shown in FIG. 8 demonstrate that all the groups show equally high levels of antibody titer regardless of the order in which a chitosan solution, an additive solution, and an antigen solution are mixed.

Example 9: Antibody Production in Rat

For study of antibody production effect in various kinds of animals, each of the following groups was evaluated for titer of antigen-specific antibody after the second immunization of rats.
(Test Materials)
<Tested Animal>
Female SD rats were used.
<Immunizing Antigen>
Test solutions were administered to the rats via various administration routes. Rats 1 and 2 (comparative examples) received intramuscular administration of Freund's adjuvant, Rats 3 and 4 received intramuscular administration of dextran-branch chitosan (FL80-Dex+OA) micronized with sodium oleate (OA), and Rat 5 received subcutaneous administration of dextran-branch chitosan (FL80-Dex+OA) micronized with sodium oleate (OA).

Figure 9:
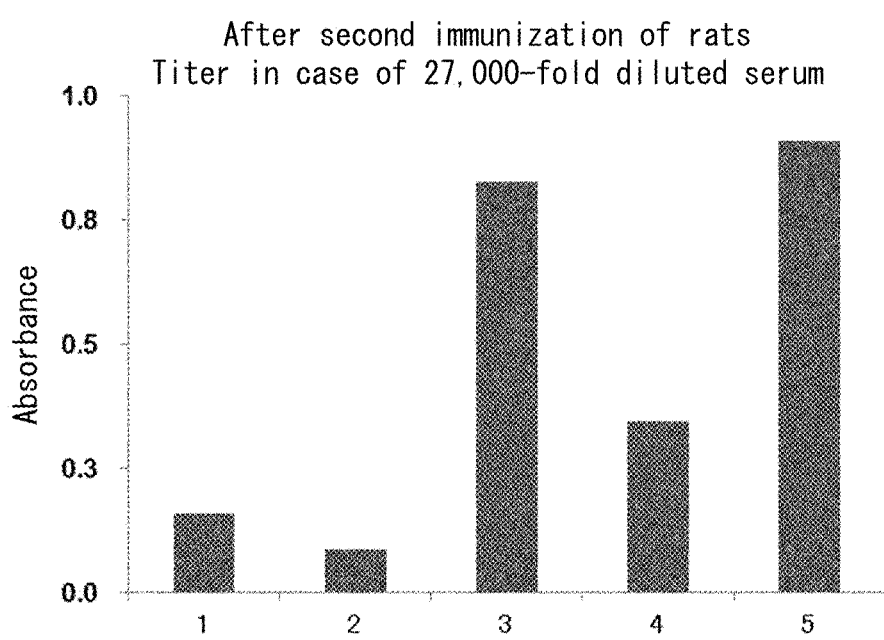
FIG. 9 shows antibody titers after the intramuscular or subcutaneous administration of a micronized chitosan derivative to rats, in accordance with Example 9 of the present invention.

The antigen solution used for Rats 1 and 2 was the same as that used for Group 1 of Example 3, and the antigen solution used for Rats 3 to 5 was the same as that used for Group 5 of Example 3. The amount of administration of the solution was 100 per rat. The immunization schedule was such that, after the first immunization, booster immunizations were carried out in the same manner at 2-week intervals. Blood was collected from tail vein one week after every booster immunization, and blood serum was obtained. The method of determining antibody titer was the same as that described in Example 3. The antibody titers of IgG against OVA after the second immunization, thus obtained, are shown in FIG. 9. As shown in the results of FIG. 9, sufficient antibody production was verified also in rats, as with mice. The sufficient antibody production was obtained both in the case of intramuscular administration and in the case of subcutaneous administration.

Example 10: Antibody Production in Rabbits

For study of antibody production effect in various kinds of animals, each of the following groups was evaluated for titer of antigen-specific antibody after immunizations of rabbits.
(Test Materials)
<Tested Animal>
Female Japanese White Rabbits were used.
<Immunizing Antigen>
Test solutions were administered to the rabbits via various administration routes. Rabbits 1 and 2 (comparative examples) received intramuscular administration of Freund's adjuvant, Rabbits 3 and 4 received intramuscular administration of dextran-branch chitosan (FL80-Dex+OA) micronized with sodium oleate (OA), and Rabbit 5 received subcutaneous administration of dextran-branch chitosan (FL80-Dex+OA) micronized with sodium oleate (OA).

Figure 10:
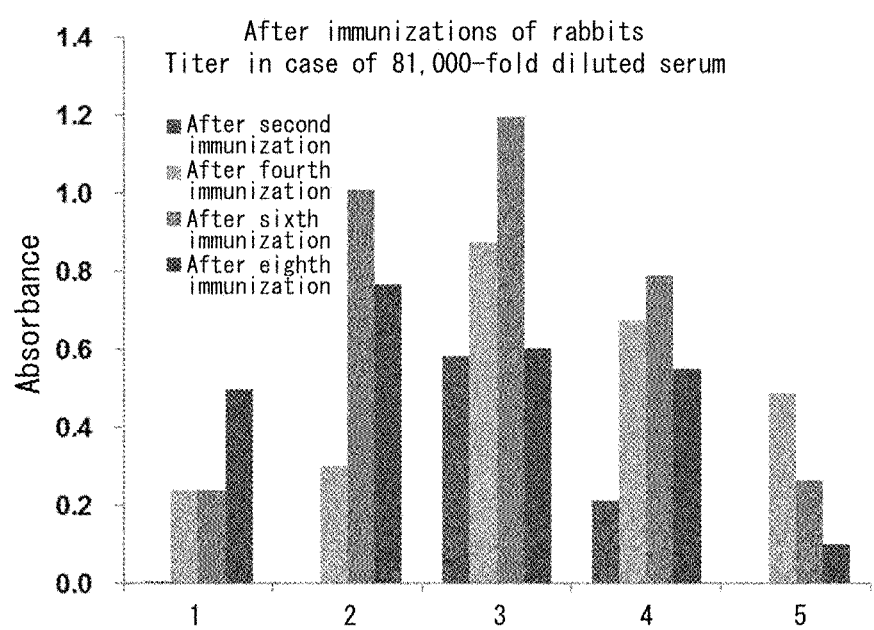
FIG. 10 shows antibody titers after the intramuscular or subcutaneous administration of a micronized chitosan derivative to rabbits, in accordance with Example 10 of the present invention.

The antigen solution used for Rabbits 1 and 2 was the same as that used for Group 1 of Example 3, and the antigen solution used for Rabbits 3 to 5 was the same as that used for Group 5 of Example 3. The amount of administration of the solution was 100 µL per rabbit. The immunization schedule was such that, after the first immunization, booster immunizations were carried out in the same manner at 2-week intervals. Blood was collected from tail vein one week after every booster immunization, and blood serum was obtained. The method of determining antibody titer was the same as that described in Example 3. The antibody titers of IgG against OVA thus obtained are shown in FIG. 10. It was verified from the results of FIG. 10 that sufficient antibody production occurs also in rabbits.

Example 11: Antiviral Immunity in Chickens

For study of antibody production effect in various kinds of animals, and for verification of immunity against viral antigens, each of the following groups was evaluated for titer of antigen-specific antibody and neutralizing antibody titer after the second or third immunization of chickens.
(Test Materials)
<Tested Animal>
Two-week-old SPF chickens, Line-M (White Leghorn, male-female mixed) were selected into groups by stratified random sampling so that the groups would be even in body weight and male/female ratio. The chickens were sampled so that each group would include five to six chickens.

<Immunizing Antigen>
Test solutions were administered to Groups 1 to 3. PBS was used for Group 1 (control group), nonderivative chitosan (FL80+OA) micronized with sodium oleate was used for Group 2, and Freund's adjuvant was used for Group 3. For Group 2, the final concentration of chitosan was 0.1%, the buffer used was an acetate buffer (pH5.0, in physiological saline) and the final concentration was 50 mM, and the amount of the additive added was 0.25 equivalents of the chitosan's amino group. Each test solution was prepared by inactivating infectious bursal disease (IBD) virus, Lukert strain (the concentration of the virus before inactivation was $10^{6.48}$ PFU/mL) with β-propiolactone to obtain an antigen solution, and mixing the antigen solution with each adjuvant at a ratio of 1:1 in each of Groups 2 and 3. The dose was 200 µL per chicken at the first immunization and 500 µL (aliquots of 250 µL to two different positions) at each of the second and subsequent immunizations. The solution was intramuscularly administered in a leg portion.

(Test Method)
<Immunization Schedule>
For all the chickens, the first immunization was carried out when they were two weeks old. For all the chickens, the second immunization was carried out when they were seven weeks old. For all the chickens in Group 1 and for half of the chickens in each of Groups 2 and 3, the third immunization was carried out when they were ten weeks old (all administered intramuscularly in leg portion). Blood was collected from them when they were six, nine, ten, and twelve weeks old, and blood serum was obtained.

<Determination of Antibody Titer>
ELISA testing was carried out with the use of an IBD ELISA kit IDEXX IBD (available from IDEXX Laboratories, Inc.) in accordance with the protocol.

The determination of neutralizing antibody titer was carried out in the following manner. The blood serum from twelve-year-old chickens was decomplementized at 56° C. for 30 minutes, and 2-fold serially diluted with the use of a blood serum diluent liquid to obtain diluted solutions. A virus fluid for neutralization test containing 100 to 200 PFU per 0.1 mL was mixed in an amount equivalent to each diluted solution, and treated at 4° C. for 18 to 24 hours. In the same manner, a mixture of equivalents of the virus flood and the blood serum diluent liquid was prepared as a virus control. Each mixture was inoculated in aliquots of 0.1 mL to two chick embryo fibroblast (CEF) cells, allowed to stand at 5% $CO_2$, 37° C. for 60 minutes, and then a primary overlay agar medium was overlaid and maintained in static culture for 3 to 4 days under the same conditions. Then, a secondary overlay agar medium was overlaid, and maintained in static culture for another 6 to 18 hours under the same conditions, and observed. The maximum dilution multiple of the blood serum to reduce the number of plaques by 50% compared to the virus control was used as a neutralizing antibody titer.

The results of the ELISA of IBD antibody and the neutralizing antibody titers thus obtained are shown in Table 1. The results shown in Table 1 demonstrate that the group immunized with chitosan microparticles of the present invention shows a significantly higher antibody titer than the group immunized with Freund's adjuvant.

TABLE 1

Chicken anti-IBD virus immunoassay

| Group | Male/female | Wing band No. | Number of immunizations | ELISA | Neutralizing antibody titer (-fold) |
|---|---|---|---|---|---|
| Control Group (Group 1) | Female | 581 | 3 | 0 | <5 |
|  | Male | 587 |  | 0 | <5 |
|  | Female | 595 |  | 0 | <5 |
|  | Female | 995 |  | 0.01 | <5 |
|  | Female | 999 |  | 0 | <5 |
| Chitosan-microparticles-administered group (Group 2) | Male | 579 | 3 | 2.76 | 204,800 |
|  | Female | 590 |  | 0.5 | 6,400 |
|  | Female | 998 |  | 0.73 | 25,600 |
|  | Female | 584 | 2 | 0.04 | 102,400 |
|  | Male | 591 |  | 0.09 | 6,400 |
|  | Male | 599 |  | 0.27 | 1,600 |
| FCA-administered group (Group 3) | Female | 597 | 3 | 0.77 | 100 |
|  | Female | 993 |  | 0.08 | <100 |
|  | Male | 996 |  | 0.13 | 400 |
|  | Male | 600 | 2 | 0.05 | 1,600 |
|  | Female | 994 |  | 0 | 1,600 |
|  | Male | 1000 |  | 0.04 | <100 |

Example 12: Effect of Frequent Administration on Mouse

For evaluation of the effect of frequent administration of a particulate chitosan adjuvant and for evaluation of changes of antibody titer, each of the following groups was evaluated for titer of antigen-specific antibody in mice.

(Test Materials)
<Tested Animal>

In the same manner as described in Example 2, five-week-old female Balb/c mice were randomly selected into groups such that each group would include five mice, after one week of habituation.

<Immunizing Antigen>

The mice thus grouped into Groups 1 and 2 received administration of the following test solutions, and were used in the following experiments. Freund's adjuvant was used for Group 1 as a comparative example, and nonderivative chitosan (FL-80+OA) micronized with sodium oleate was used for Group 2. The antigen solution used for Group 1 was the same as that used for Group 1 of Example 3. The antigen solution used for Group 2 was the same as that used for Group 4 of Example 3. The amount of administration of the solution was 100 µL per mouse. Ovalbumin (OVA) as an antigen solution was mixed into the test solution for each group so that the dose of the antigen would be 1 µg per mouse. The same immunization schedule as that of Example 3 was followed, and blood was collected from tail vein one week after every booster immunization at 2-week intervals, and blood serum was obtained. The method of determining antibody titer was the same as that of Example 3.

Figure 11:
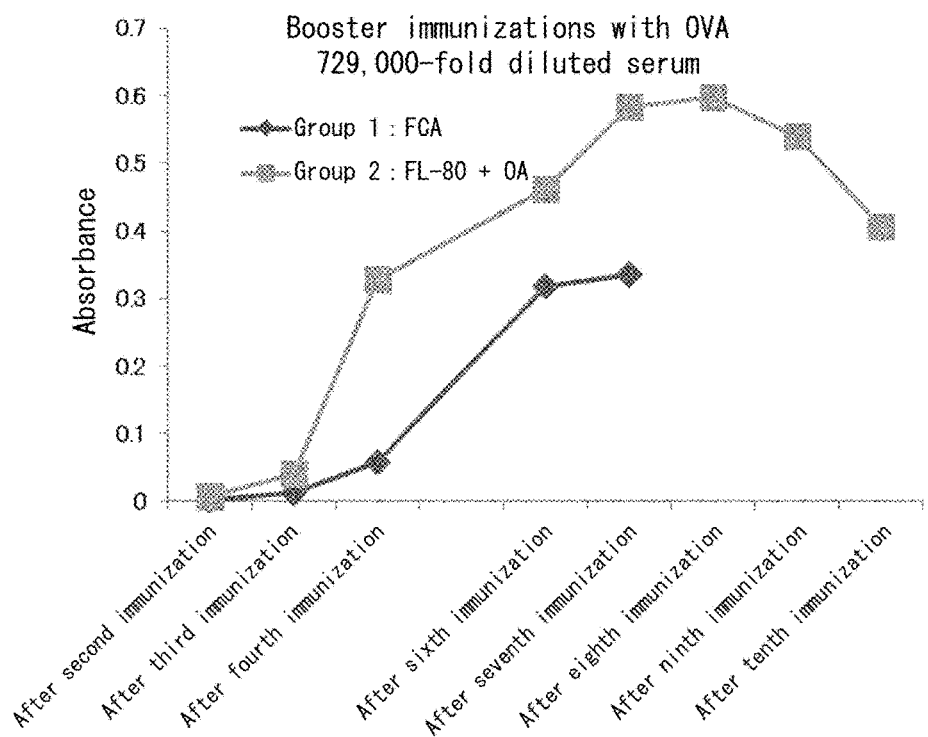
FIG. 11 shows antibody titers after the intraperitoneal administration of a micronized chitosan derivative to mice, in accordance with Example 12 of the present invention.

The antibody titers of IgG against OVA thus obtained are shown in FIG. 11. In FIG. 11, the horizontal axis shows the number of immunizations, and the vertical axis shows absorbance. The results shown in FIG. 11 demonstrate that the group immunized with chitosan microparticles shows a significantly higher antibody titer than the group immunized with Freund's adjuvant.

Figure 12:
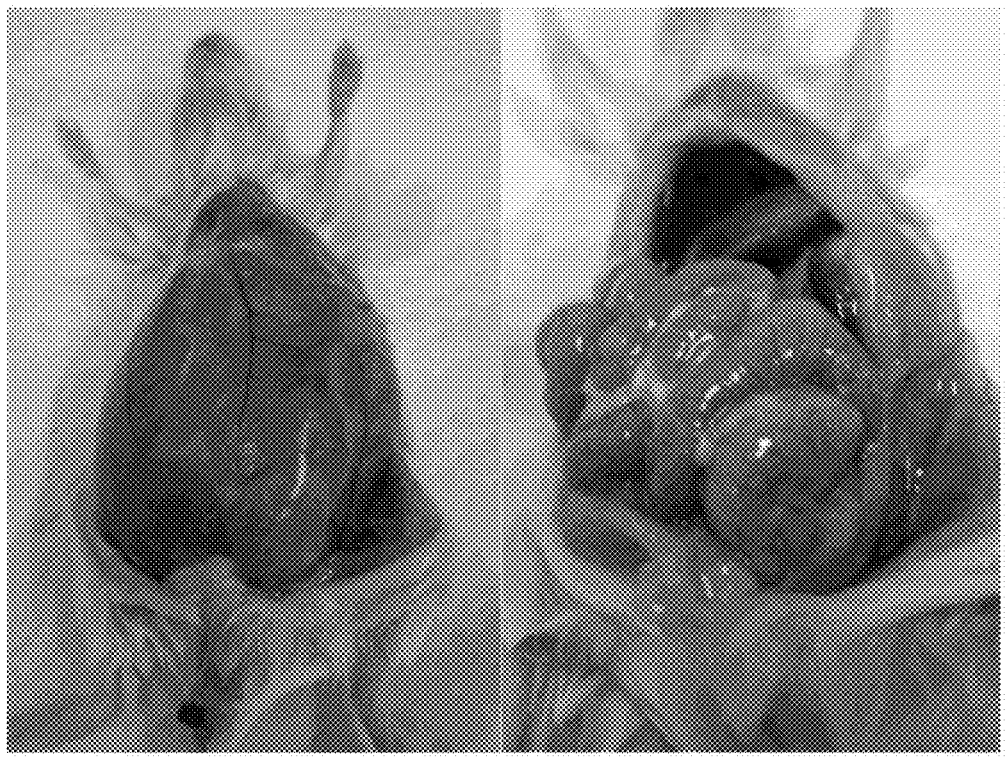
FIG. 12 shows the results of an autopsy on a mouse after the seventh immunization with Freund's adjuvant, in accordance with Example 12 of the present invention.

Furthermore, an autopsy was carried out on an immunized mouse, and the inside of the abdominal cavity was checked. As a result, no abnormalities were found in the mouse in the group immunized with chitosan microparticles, even after the tenth immunization (not shown). On the other hand, a mouse after receiving the seventh immunization with Freund's adjuvant suffered from abdominal swelling due to a large amount of ascitic fluid as shown in FIG. 12, and a residue of the adjuvant was found.

INDUSTRIAL APPLICABILITY

A chitosan derivative in accordance with the present invention has immunostimulatory activity and can be used as an immunostimulator. Microparticles that contain a [chitosan and/or chitosan derivative] and an anionic surfactant in accordance with the present invention can be used as an immunostimulator.

The invention claimed is:

1. An immunostimulator comprising:
chitosan and/or a chitosan derivative each having a weight-average molecular weight of 10k to 1000k; and
an anionic surfactant, wherein the anionic surfactant is at least one selected from the group consisting of C10-C22 fatty acids, and salts of the C10-C22 fatty acids,
the immunostimulator being in particulate form,
wherein the chitosan and/or the chitosan derivative and an ionic surfactant are complexed via an electrostatic interaction,
wherein the chitosan derivative has immunostimulatory activity and is represented by General Formula (I) below:

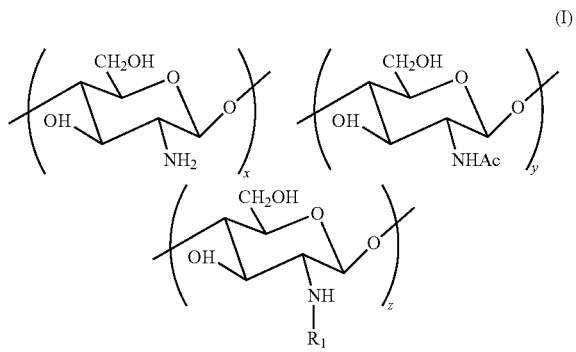

where
x, y, and z represent respective molar proportions which satisfy the equation x+y+z=1, where $0 \leq x < 1$, $0 \leq y < 1$, and $0 < z \leq 1$, and
$R^1$ is a pullulan side chain represented by General Formula (II) below:

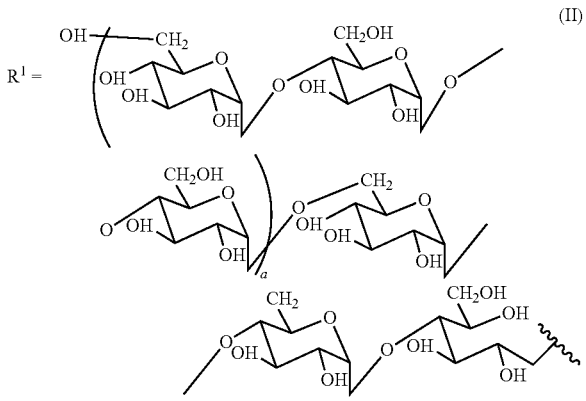

where a represents an integer of 20 to 600, a degree of substitution with the pullulan side chain being 0.001 to 0.1, a dextran side chain represented by General Formula (III) below:

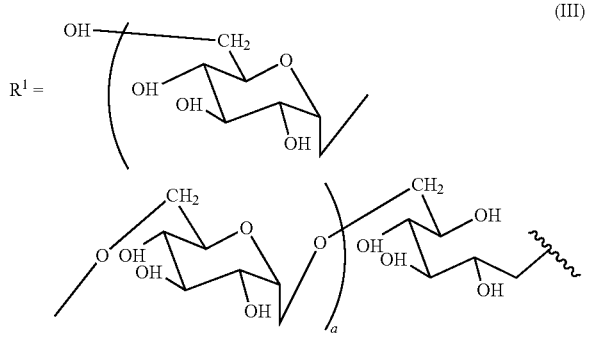

(III)

where a represents an integer of 15 to 300, a degree of substitution with the dextran side chain being 0.001 to 0.1, a glucosamine side chain represented by General Formula (IV) below:

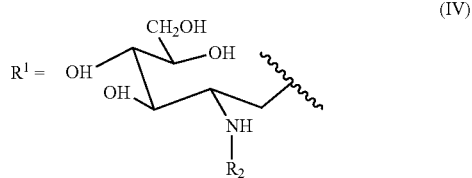

(IV)

where $R^2$ represents an acetyl group, a degree of substitution with the glucosamine side chain being 0.05 to 0.5, or a lysine side chain represented by General Formula (V) below:

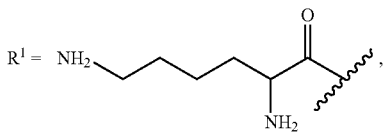

(V)

a degree of substitution with the lysine side chain being 0.02 to 0.5, wherein the number of the saccharide units in General Formula (I) falls within the range of from 60 to 6,000, wherein a molar ratio of (i) amino groups of the chitosan and/or the chitosan derivative to (ii) carboxyl groups of the anionic surfactant, per particle of the immunostimulator in particulate form, is 1:0.05 to 1:1.

2. The immunostimulator according to claim 1, wherein: the C10-C22 fatty acids and the salts of the C10-C22 fatty acids are selected from the group consisting of sodium oleate and sodium laurate.

3. The immunostimulator according to claim 1, wherein z in General Formula (I) is 0.001 to 0.5.

4. A pharmaceutical composition comprising, as an active ingredient, an immunostimulator as set forth in claim 1.

5. An alimentary product comprising an immunostimulator as set forth in claim 1.

6. A method of stimulating immune activity of a living body, comprising the step of administering a pharmaceutical composition as set forth in claim 4.

7. A method of stimulating immune activity of a living body, comprising the step of administering an alimentary product as set forth in claim 5.

* * * * *

UNITED STATES PATENT AND TRADEMARK OFFICE
CERTIFICATE OF CORRECTION

PATENT NO. : 11,559,543 B2
APPLICATION NO. : 16/321781
DATED : January 24, 2023
INVENTOR(S) : Etsuya Okamoto and Hiroaki Kodama It is certified that error appears in the above-identified patent and that said Letters Patent is hereby corrected as shown below:

In the Claims

Column 36, Claim 1, Line 59 & 62 reads:

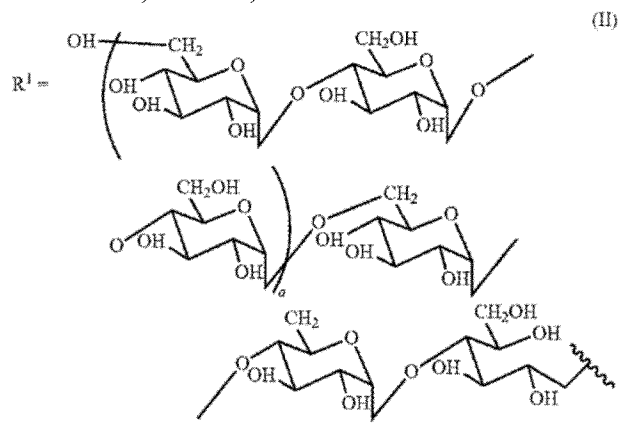

Whereas it should read:

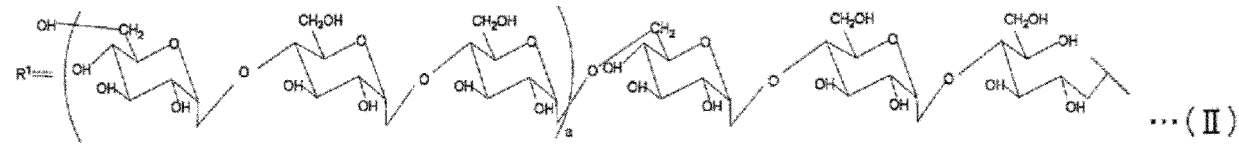

Signed and Sealed this
Sixth Day of June, 2023

Katherine Kelly Vidal
*Director of the United States Patent and Trademark Office*